US010285976B2

(12) United States Patent
Bollyky et al.

(10) Patent No.: US 10,285,976 B2
(45) Date of Patent: May 14, 2019

(54) 4-METHYLUMBELLIFERONE TREATMENT FOR IMMUNE MODULATION

(71) Applicants: Benaroya Research Institute at Virginia Mason, Seattle, WA (US); The Board of Trustees of the Leland Stanford Junior University, Palo Alto, CA (US)

(72) Inventors: Paul L. Bollyky, Palo Alto, CA (US); Nadine Nagy, Seattle, WA (US); Thomas Wight, Seattle, WA (US); Hedwich F. Kuipers, Palo Alto, CA (US)

(73) Assignees: THE BOARD OF TRUSTEES OF THE LELAND STANFORD JUNIOR UNIVERSITY, Palo Alto, CA (US); BENAROYA RESEARCH INSTITUTE AT VIRGINIA MASON, Seattle, WA (US)

( * ) Notice: Subject to any disclaimer, the term of this patent is extended or adjusted under 35 U.S.C. 154(b) by 0 days.

(21) Appl. No.: 14/911,533

(22) PCT Filed: Aug. 12, 2014

(86) PCT No.: PCT/US2014/050770
§ 371 (c)(1),
(2) Date: Feb. 11, 2016

(87) PCT Pub. No.: WO2015/023691
PCT Pub. Date: Feb. 19, 2015

(65) Prior Publication Data
US 2016/0184262 A1 Jun. 30, 2016

Related U.S. Application Data

(60) Provisional application No. 61/865,084, filed on Aug. 12, 2013.

(51) Int. Cl.
*A61K 31/37* (2006.01)
*A61K 31/7048* (2006.01)

(52) U.S. Cl.
CPC .......... *A61K 31/37* (2013.01); *A61K 31/7048* (2013.01)

(58) Field of Classification Search
None
See application file for complete search history.

(56) References Cited

U.S. PATENT DOCUMENTS

| 6,376,475 B1 | 4/2002 | Marth | |
| 6,407,073 B1* | 6/2002 | Trkovnik | A61K 31/37 514/27 |
| 2005/0118157 A1* | 6/2005 | McMahon | A61K 31/70 424/94.61 |
| 2008/0152640 A1 | 6/2008 | Prehm | |
| 2012/0219506 A1 | 8/2012 | Moore | |
| 2013/0302400 A1* | 11/2013 | Maneval | A61K 38/47 424/450 |

FOREIGN PATENT DOCUMENTS

| CN | 102846598 A | 1/2013 |
| JP | 2004-517030 A | 6/2004 |
| JP | 2005-530778 A | 10/2005 |
| WO | 2001/068095 A1 | 9/2001 |
| WO | 03/097024 A1 | 11/2003 |
| WO | 2004/082610 A2 | 9/2004 |
| WO | 2012/012300 A2 | 1/2012 |

OTHER PUBLICATIONS

Yoshioka, Y., Kozawa, E., Urakawa, H., Arai, E., Futamura, N., Zhuo, L., . . . & Nishida, Y. (2013). Suppression of hyaluronan synthesis alleviates inflammatory responses in murine arthritis and in human rheumatoid synovial fibroblasts. Arthritis & Rheumatism, 65(5), 1160-1170.*
Chan, D. T. M., Tse, W. W., Chau, M., & Yung, S. (2011). Suppression of hyaluronan synthesis with 4-methylumbelliferone in NZB/W F1 mice is associated with reduced renal inflammation and renal function improvement. Journal of the American Society of Nephrology.*
Kakizaki, I., Kojima, K., Takagaki, K., Endo, M., Kannagi, R., Ito, M., . . . & Kimata, K. (2004). A novel mechanism for the inhibition of hyaluronan biosynthesis by 4-methylumbelliferone. Journal of Biological Chemistry, 279(32), 33281-33289.*
Michishi et al., JP 2008195703 A, Aug. 2008, original and machine translation, Retreived on Jun. 9, 2013 from http://worldwide.espacenet.com.*
Bollyky, P. L. Bogdani, M., Bollyky, J. B., Hull, R. L., & Wight, T. N. (2012). The role of hyaluronan and the extracellular matrix in islet inflammation and immune regulation. Current diabetes reports, 12(5), 471-480.*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Goldenberg, M. M. (2012). Multiple sclerosis review. Pharmacy and Therapeutics, 37(3), 175. (Year: 2012).*
Singh, P., Sharma, P. K., Garg, V. K., kumar Singh, A., & Mondal, S. C. A review on prevalence of latent autoimmune diabetes in adults. (2011) (Year: 2011).*

(Continued)

*Primary Examiner* — Shaojia A Jiang
*Assistant Examiner* — Dale R Miller
(74) *Attorney, Agent, or Firm* — Christensen O'Connor Johnson Kindness PLLC

(57) ABSTRACT

Compositions for treating autoimmune, allergic, or atopic disease comprising a compound that inhibits hyaluronan synthesis and a pharmaceutically acceptable carrier are described. In some embodiments, the compound that inhibits hyaluronan synthesis is 4-methylumbelliferone or a metabolite of 4-methylumbelliferone. Methods for treating autoimmune diabetes, multiple sclerosis and/or autoimmune demyelination, including administering to the subject a composition having a compound in an amount effective to inhibit hyaluronan synthesis in a mammalian subject, are also described.

23 Claims, 21 Drawing Sheets

(56) References Cited

OTHER PUBLICATIONS

Kultti, A. et al, "4-Methylumbelliferone Inhibits Hyaluronan Synthesis by Depletion of Cellular UDP-Glucuronic Acid and Downregulation of Hyaluronan Synthase 2 and 3," Experimental Cell Research, 315(11): 1914-1923, Jul. 1, 2009.

International Search Report and Written Opinion dated Jan. 22, 2015, in corresponding International Application No. PCT/US2014/050770, filed Aug. 12, 2014, 4 pages.

International Preliminary Report on Patentability dated Feb. 16, 2016, in corresponding International Application No. PCT/US2014/050770, filed Aug. 12, 2014, 5 pages.

Notice of Reasons for Rejection dated May 1, 2018, issued in Japanese Application No. 2016-534801, filed Aug. 12, 2014, 9 pages.

Nagy, N., et al., "Inhibition of Hyaluronan Synthesis Accelerates Murine Atherosclerosis," Circulation 122(22):2313-2322, Nov. 2010.

Communication dated Aug. 2, 2018, issued in EP Application No. 14836423.5, filed Aug. 12, 2014, 8 pages.

Lawrence Woo, L.W., et al., "Active Site Directed Inhibition of Estrone Sulfatase by Nonsteroidal Coumarin Sulfamates," Journal of Medicinal Chemistry 39(7):1349-1351, Mar. 1996.

Sainio, A., et al., "Hyperglycemic Conditions Modulate Connective Tissue Reorganization by Human Vascular Smooth Muscle Cells Through Stimulation of Hyaluronan Synthesis," Glycobiology 20(9):1117-1126, Sep. 2010.

Notification of the First Office Action dated Sep. 28, 2018, issued in CN Application No. 201480053371.4, filed Aug. 12, 2014, 23 pages.

Extended European Search Report dated Jan. 9, 2017, issued in EP Application No. 14836423.5, filed Aug. 12, 2014, 34 pages.

\* cited by examiner

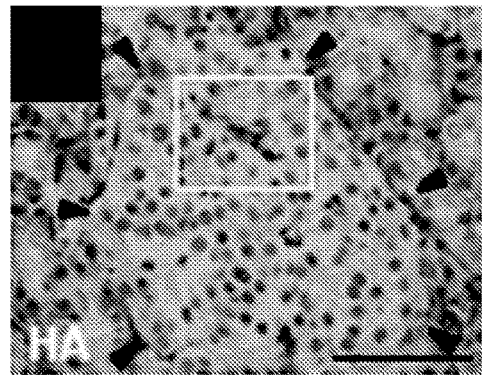
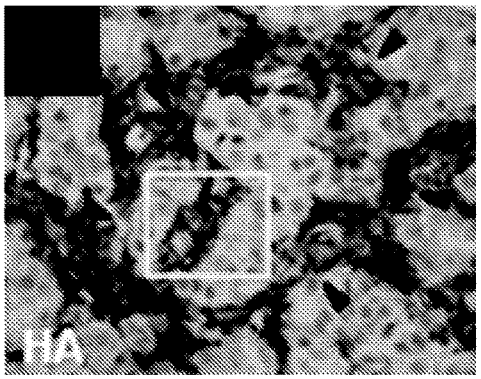
FIG. 2A  FIG. 2B
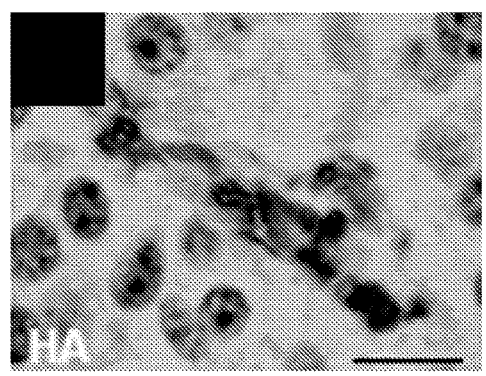
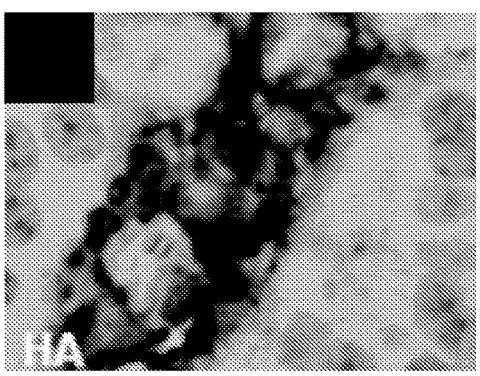
FIG. 2C  FIG. 2D

4-METHYLUMBELLIFERONE TREATMENT FOR IMMUNE MODULATION

CROSS-REFERENCE TO RELATED APPLICATION

This application claims the benefit of U.S. Provisional Application No. 61/865,084, filed Aug. 12, 2013, which is incorporated herein by reference.

STATEMENT OF GOVERNMENT LICENSE RIGHTS

This invention was made with Government support under contracts AI101984 and DK096087 awarded by the National Institutes of Health. The Government has certain rights in this invention.

FIELD OF THE INVENTION

The present disclosure relates to immunomodulatory compositions and methods of using the compositions to inhibit hyaluronan synthesis. The disclosure also relates to compositions and methods for treating an autoimmune disease or disorder such as diabetes or multiple sclerosis.

BACKGROUND

An autoimmune disease or disorder occurs when the body's immune system attacks and destroys healthy body tissue by mistake. Autoimmune diseases can attack almost any tissue in the body and all autoimmune diseases are characterized by local inflammation and infiltration by immune cells called lymphocytes.

As an example, autoimmune diabetes, also known as Type 1 diabetes or insulin-dependent diabetes mellitus (IDDM), occurs when the body's immune system mistakenly destroys the pancreatic cells, called beta cells, that make insulin. Damage to beta cells results in an absence or insufficient production of insulin produced by the body. In all autoimmune diseases, including autoimmune diabetes, lymphocytes migrate from the blood stream into target tissues via interactions with the extracellular matrix (ECM). In the case of autoimmune diabetes, lymphocytes attack pancreatic islets via interaction with ECM that lies between islet capillaries and endocrine cells.

One in three hundred American children will develop autoimmune diabetes. Many of these individuals can be identified before they present with hyperglycemia through screening for autoimmune diabetes associated autoantibodies. Thus, there is a therapeutic window where autoimmune diabetes could be prevented, given the knowledge and means to do so. The present application describes novel strategies to reverse and/or prevent the progression to autoimmune diabetes in at-risk individuals.

As another example, multiple sclerosis (MS) is also an autoimmune disease but in MS the autoimmune activity is directed against central nervous system (CNS) antigens. The disease is characterized by inflammation in parts of the CNS, leading to the loss of the myelin sheathing around neuronal axons (demyelination), axonal loss, and the eventual death of neurons, oligodendrocytes and glial cells. For a comprehensive review of MS and current therapies, see, e.g., Compston, A., et al., *McAlpine's Multiple Sclerosis* 4th ed., Churchill Livingstone Elsevier (2006).

MS is one of the most common diseases of the CNS in young adults, and an estimated 2.5 million people suffer from MS. MS is a chronic, progressing, disabling disease, which generally strikes its victims sometime after adolescence, with diagnosis generally made between 20 and 40 years of age, although onset can occur earlier. The disease is not directly hereditary, although genetic susceptibility plays a part in its development. MS is a complex disease with heterogeneous clinical, pathological and immunological phenotype.

There are four major clinical types of MS: 1) relapsing-remitting MS (RRMS), characterized by clearly defined relapses with full recovery or with sequelae and residual deficit upon recovery; periods between disease relapses are characterized by a lack of disease progression; 2) secondary progressive MS (SPMS), characterized by an initial relapsing remitting course followed by progression with or without occasional relapses, minor remissions, and plateaus; 3) primary progressive MS (PPMS), characterized by disease progression from onset with occasional plateaus and temporary minor improvements allowed; and 4) progressive relapsing MS (PRMS), characterized by progressive disease onset, with clear acute relapses, with or without full recovery; periods between relapses characterized by continuing progression.

Clinically, the illness most often presents as a relapsing-remitting disease and, to a lesser extent, as steady progression of neurological disability. Relapsing-remitting MS presents in the form of recurrent attacks of focal or multifocal neurologic dysfunction. Attacks can occur, remit, and recur, seemingly randomly over many years. Remission is often incomplete and as one attack follows another, a stepwise downward progression ensues with increasing permanent neurological deficit. The usual course of RRMS is characterized by repeated relapses associated, for the majority of patients, with the eventual onset of disease progression. The subsequent course of the disease is unpredictable, although most patients with a relapsing-remitting disease will eventually develop secondary progressive disease. In the relapsing-remitting phase, relapses alternate with periods of clinical inactivity and may or may not be marked by sequelae depending on the presence of neurological deficits between episodes. Periods between relapses during the relapsing-remitting phase are clinically stable. On the other hand, patients with progressive MS exhibit a steady increase in deficits as defined above and either from onset or after a period of episodes, but this designation does not preclude the further occurrence of new relapses.

In healthy individuals (i.e., those without an autoimmune disease or disorder), immune tolerance is maintained by populations of regulatory T-cells including FoxP3+ regulatory T-cells (Treg) (Sakaguchi, S., et al., *Nat. Rev. Immunol.* 10, 490-500 (2010)). Treg absence or depletion leads to multi-systemic autoimmunity in mice and humans (Wildin, R. S., et al., *Nat. Genet.* 27, 18-20 (2001)) whereas adoptive transfer of Treg can abrogate autoimmunity.

In MS, Treg present in the CNS are known to limit the extent of neuroinflammation and to facilitate clinical recovery during the mouse model of multiple sclerosis, experimental autoimmune encephalomyelitis (EAE), such that multiple investigative therapeutic strategies to treat autoimmune demyelination are directed at promoting the number and/or function of Treg. However, existing therapies have not managed to induce stable, functional FoxP3+ Treg, in part because Treg in vivo are a population in flux. Natural Treg (nTreg) continually emerge through thymic selection, whereas induced Treg (iTreg) originate in peripheral tissues in response to inflammatory stimuli and can revert into effector T-cells. This variability in the number and function of local Treg at sites of inflammation can impact the durability of immune tolerance in peripheral tissues.

Despite the fact that the inflammatory milieu is known to have decisive effects on immune tolerance, little is known about how the tissue micro-environment influences the function and number of Treg. Therefore, there is increasing interest in the role of ECM at the interface between lymphocytes and local cells in autoimmunity (Bollyky, P. L., et al., *Curr. Diab. Rep.* 12, 471-480 (2012); Irving-Rodgers, H. F., et al., *Diabetologia* 51, 1680-1688 (2008); Hull, R. L., et al., *J. Biol. Chem.* 287, 37154-37164 (2012); Bitan, M., et al., *Diabetes. Metab. Res. Rev.* 24, 413-421 (2008); Ziolkowski, A. F., et al., *J. Clin. Invest.* 122, 132-141 (2012)).

One tissue component that is abundant at sites of inflammation is hyaluronan (HA), an extracellular matrix (ECM) polysaccharide. HA has many functions, such as providing support and anchorage for cells, segregating tissues from one another, facilitating cell to cell signaling, development, migration and function (Bollyky, P. L., et al. (2012), supra). HA is synthesized by a class of integral membrane proteins called hyaluronan synthases and extruded through the cell membrane into the extracellular space (Laurent, T. C., et al., *Immunol. Cell Biol.* 74, A1-7 (1996)).

HA is a polymer of disaccharides composed of glucuronic acid and N-acetylglucosamine and linked via alternating β-1,4 and β-1,3 glycosidic bonds. HA can be 25,000 disaccharide repeats in length. In vivo polymers of HA can range in size from 5,000 to 20,000,000 Da. HA is synthesized by a class of integral membrane proteins called hyaluronan synthases, of which vertebrates have three types: HAS1, HAS2, and HAS3. These enzymes lengthen hyaluronan by repeatedly adding glucuronic acid and N-acetylglucosamine to the nascent polysaccharide as it is extruded through the cell membrane into the extracellular space.

HA is a key mediator of inflammation, with roles in lymphocyte trafficking, proliferation, and antigen presentation (Laurent, T. C., and Fraser, J. R., *FASEB J.* 6, 2397-2404 (1992); Bollyky, P. L., et al., *Cell Mol Immunol.* 3, 211-220 (2010)). HA is increased in lesions associated with human autoimmune diseases, including multiple sclerosis, Sjögrens disease, and autoimmune thyroiditis (Back, S. A., et al., *Nat. Med.* 11, 966-972 (2005); Engström-Laurent, A. "Changes in hyaluronan concentration in tissues and body fluids in disease states." *The Biology of Hyaluronan*, CIBA Foundation Symposium, 143, 233-47 (1989); Gianoukakis, A., et al., *Endocrinology* 148, 54-62 (2007). HA is also increased in the serum of individuals with Lupus, rheumatoid arthritis, psoriasis, and autoimmune thyroiditis (Engström-Laurent, supra; Pitsillides et al., *Rheumatol.* 33, 5-10 (1994); Hansen, C., et al., *Clin. Exp. Rheumatol.* 14 Suppl. 15, S59-67 (1996); Torsteinsdottir et al., *Clin. Exp. Immunol.* 115, 554-560 (1999); Elkayam, O., et al., *Clin. Rheumatol.* 19, 455-457 (2000); Kubo, M., et al., *Arch. Dermatol. Res.* 290, 579-581 (1998).

HA is highly abundant within chronically inflamed tissues, including for example MS lesions (Bollyky, P. L., et al. (2012), supra; Back, S. A., et al., supra). For example, in one study HA was shown to accumulate in demyelinated lesions in MS and EAE. Immunostaining for PLP of a chronic MS lesion showed complete loss of myelin in the center of the lesions. CD44 staining revealed high levels of CD44 in the lesions, and elevated CD44 expression in GFAP-expressing reactive astrocytes were also found. HA staining showed high levels of HA in demyelinated regions of the lesions but at lower levels in the lesion borders (Back S. A., et al., supra).

Typically, HA present within chronically inflamed tissues takes the form of short, highly catabolized fragments (as reviewed in Bollyky, P. L., et al. (2012), supra) that are pro-inflammatory agonists of Toll-like receptor signalling (Laurent, T. C., et al., *Immunol. Cell Biol.* 74, A1-7 (1996); Jiang, D., et al., *Physiol. Rev.* 91, 221-264 (2011)), driving dendritic cell maturation, and promoting phagocytosis (Jiang, D., et al., *Nat. Med.* 11, 1173-1179 (2005); Termeer, C., et al., *J. Exp. Med.* 195, 99-111 (2002)). HA overexpression tends to drive inflammation (Olsson, M. et al., *PLoS Genet.* 7, e1001332 (2011)), presumably through production of increased HA fragments, while inhibition of HA synthesis, including treatment with 4-methylumbelliferone (4-MU, Hymecromone), tends to reduce inflammation (Yoshioka, Y., et al., *Arthritis Rheum.* 65, 1160-1170 (2013); McKallip, R. J., et al., *Toxins (Basel)* 5, 1814-1826 (2013); Colombaro, V. et al., *Nephrol. Dial. Transplant* 28, 2484-2493 (2013); Saito, T., et al., *Oncol. Lett.* 5, 1068-1074 (2013)). With respect to the role of HA in local immune modulation, it is known that low molecular weight HA (LMW-HA) fragments inhibit the function of FoxP3+ Treg (Bollyky, P. L., et al., *J. Immunol.* 179, 744-747 (2007); Bollyky, P. L., et al., *J. Immunol.* 183, 2232-2241 (2009)). These effects are mediated via TLR signaling and via interactions with the HA receptor CD44.

In the healthy CNS, astrocytes are the main producers of low levels of HA, depositing it as ECM complexes in the spaces between myelinated axons and between myelin sheaths and astrocyte processes (Asher, R., et al., *J. Neurosci. Res.* 28, 410-421 (1991)). Upon injury, however, reactive astrocytes produce abundant amounts of HA, which accumulate in damaged areas (Back, S. A., et al., supra; Struve, J., et al., *Glia* 52, 16-24 (2005); Bugiani, M., et al., *Brain* 136, 209-222 (2013)). As such, HA is present at high levels in demyelinating lesions in MS patients and in mice with EAE (Back, S. A., et al., supra).

4-MU is a selective inhibitor of HA synthesis. The compound was first used in vitro in 1995 by Nakamura et al., to inhibit HA-synthesis in skin fibroblasts. Nakamura, T., et al., *Biochem. Biophys. Res. Commun.* 208, 470-475 (1995). In 2004, the mechanism of 4-MU was discovered by Kakizaki et al., and since then it has been used in in vivo studies in mice and rats to investigate the 4-MU influence, mainly in cancer studies (Kakizaki, I., et al., *J. Biol. Chem.* 279, 33281-33289 (2004); see also, e.g., Yoshihara, S., et al., *FEBS Letters* 579, 2722-2726 (2005); Lokeshwar, V. B., et al., *Cancer Res.* 70, 2613-2623 (2010)) and in atherosclerosis studies (Nagy, N., et al., *Circulation* 122, 2313-2322 (2010)). 4-MU is also already used in humans. It is available without a prescription as Heparvit, a nutraceutical product for cancer patients. Furthermore, it is available with prescription in Europe and Asia to treat biliary spasm under the name Hymecromone. In that setting, the drug has an excellent safety profile and has been used for several years.

Although it is known that HA deposits are abundant in chronically inflamed tissues and that 4-MU is a selective inhibitor of HA synthesis, there remains a need to develop a safe and effective therapy for autoimmune diseases and disorders such as, for example, diabetes and MS, by providing a well-founded understanding of the role of HA in autoimmune pathogenesis.

SUMMARY

In one aspect, the present disclosure provides compositions for treating an autoimmune, allergic, or atopic disease comprising (i) a compound that inhibits hyaluronan synthesis, and (ii) a pharmaceutically acceptable carrier.

In one embodiment, the compound is a UDP-glycosyltransferase inhibitor. In one embodiment, the compound is a UDP-glucuronyltransferase inhibitor.

In one embodiment, the compound is 4-methylumbelliferone. In one embodiment, the compound is a metabolite of 4-methylumbelliferone. In one embodiment, the compound is 4-methylumbelliferone glucuronide or a sulfated 4-methylumbelliferone.

In one embodiment, the compound is effective to induce a regulatory T-cell response. In one embodiment, the compound is effective to increase FoxP3+ regulatory T-cells.

In one embodiment, the autoimmune, allergic, or atopic disease is selected from the group consisting of autoimmune diabetes, multiple sclerosis, Sjögrens disease, autoimmune thyroiditis, Lupus, rheumatoid arthritis, psoriasis, colitis, and asthma.

In one aspect, the present disclosure provides methods for treating an autoimmune, allergic, or atopic disease in a mammalian subject in need thereof. The method comprises administering to the subject a composition comprising a compound in an amount effective to inhibit hyaluronan synthesis in the mammalian subject.

In one embodiment, the compound is a UDP-glycosyltransferase inhibitor. In one embodiment, the compound is a UDP-glucuronyltransferase inhibitor.

In one embodiment, the compound is 4-methylumbelliferone. In one embodiment, the compound is a metabolite of 4-methylumbelliferone. In one embodiment, the compound is 4-methylumbelliferone glucuronide or a sulfated 4-methylumbelliferone.

In one embodiment, the compound is effective to induce a regulatory T-cell response. In one embodiment, the compound is effective to increase FoxP3+ regulatory T-cells.

In one embodiment, the mammalian subject is a human subject. In one embodiment, the human subject is suffering from, or at risk for developing an autoimmune, allergic, or atopic disease selected from the group consisting of autoimmune diabetes, multiple sclerosis, Sjögrens disease, autoimmune thyroiditis, Lupus, rheumatoid arthritis, psoriasis, colitis, and asthma.

In one aspect, the present disclosure provides methods for treating insulitis and/or reversing progression of autoimmune diabetes in a mammalian subject suffering from or at risk of developing autoimmune diabetes. The method comprises administering to the mammalian subject a composition comprising a compound in an amount effective to inhibit hyaluronan synthesis in the mammalian subject.

In one embodiment, the compound is a UDP-glycosyltransferase inhibitor or a UDP-glucuronyltransferase inhibitor. In one embodiment, the compound is 4-methylumbelliferone or a metabolite of 4-methylumbelliferone. In one embodiment, the mammalian subject is a human subject.

In one aspect, the present disclosure provides methods for treating multiple sclerosis in a mammalian subject in need thereof. The method comprises administering to the subject a composition comprising a compound in an amount effective to inhibit hyaluronan synthesis in the mammalian subject.

In one embodiment, the compound is a UDP-glycosyltransferase inhibitor or a UDP-glucuronyltransferase inhibitor. In one embodiment, the compound is 4-methylumbelliferone or a metabolite of 4-methylumbelliferone.

In one embodiment, the mammalian subject is a human subject. In one embodiment, the compound is effective to induce a regulatory T-cell response. In one embodiment, the compound is effective to increase FoxP3+ regulatory T-cells.

In one aspect, the present disclosure provides methods for treating multiple sclerosis and/or autoimmune demyelination in a mammalian subject suffering from or at risk of developing multiple sclerosis. The method comprises administering to the mammalian subject a composition comprising a compound in an amount effective to inhibit hyaluronan synthesis in the mammalian subject.

In one embodiment, the compound is a UDP-glycosyltransferase inhibitor or a UDP-glucuronyltransferase inhibitor. In one embodiment, the compound is 4-methylumbelliferone or a metabolite of 4-methylumbelliferone.

In one embodiment, the mammalian subject is a human subject. In one embodiment, the compound is effective to induce a regulatory T-cell response. In one embodiment, the compound is effective to increase FoxP3+ regulatory T-cells.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A shows representative HA staining of an islet from human donors without autoimmune diabetes.

FIG. 2B shows representative HA staining of an islet from human donors with autoimmune diabetes.

FIG. 2C shows representative higher magnification of intra-islet HA accumulation from human donors without autoimmune diabetes.

FIG. 2D shows representative higher magnification of intra-islet HA accumulation from human donors with autoimmune diabetes.

DETAILED DESCRIPTION

Figure 1A:
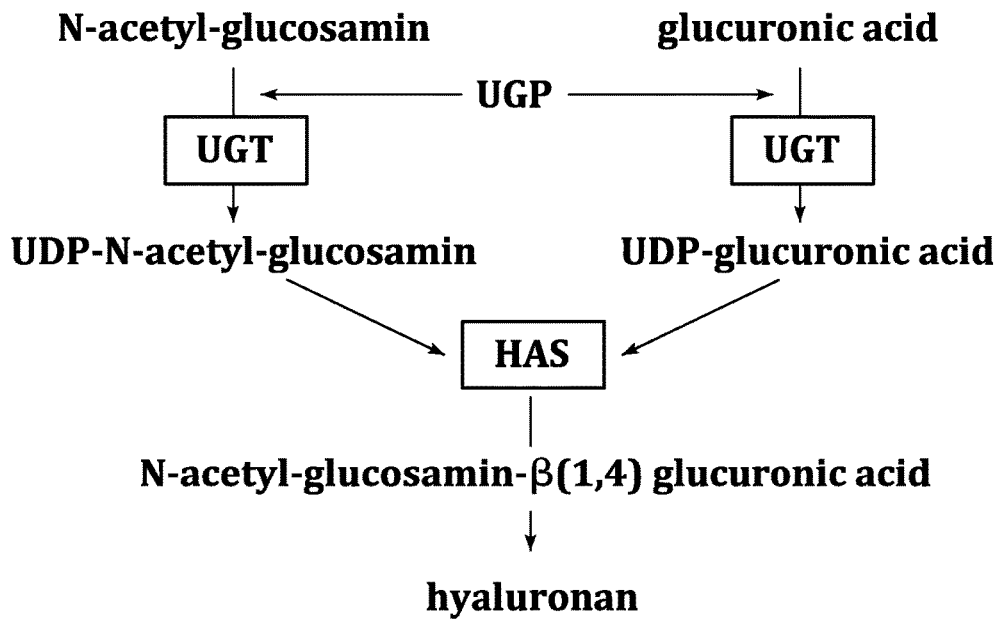
FIG. 1A illustrates a mechanism of HA synthesis.

The present disclosure describes the identification of a critical role for the extracellular matrix molecule HA in autoimmune diseases and disorders and the identification of a compound that inhibits HA synthesis, in particular 4-MU. The disclosure describes the use of 4-MU as a novel therapeutic to abrogate autoimmunity and the use of 4-MU for treating an autoimmune disease or disorder, for example, autoimmune diabetes or multiple sclerosis.

Unless specifically defined herein, all terms used herein have the same meaning as they would to one skilled in the art of the present disclosure. The following definitions are provided in order to provide clarity with respect to the terms as they are used in the specification and claims to describe the claimed subject matter.

As used herein, the term "regulatory T-cells" or "Treg" cells refers to T-cells which express the cell surface markers CD4+ and CD25+, which express FoxP3 protein as measured by a Western blot and/or FoxP3 mRNA transcript.

As used herein, the term "antigen-specific regulatory T-cells" or "antigen-specific Tregs" refers to Treg cells that were induced in the presence of an antigen and which express the cell surface markers CD4+ and CD25+, which express FoxP3 protein as measured by a Western blot and/or FoxP3 mRNA transcript.

As used herein, the term "derived from" or "a derivative thereof," in the context of peptide or polypeptide sequences, means that the peptide or polypeptide is not limited to the specific sequence described, but also includes variations in that sequence, which can include amino acid additions, deletions, substitutions, or modifications to the extent that the variations in the listed sequence retain the ability to modulate an immune response.

As used herein, the term "peptide" or "polypeptide" is a linked sequence of amino acids and can be natural, recombinant, synthetic, or a modification or combination of natural, synthetic, and recombinant.

As used herein, the expression "effective amount" or "therapeutically effective amount" refers to an amount of the compound of the present disclosure that is effective to achieve a desired therapeutic result, such as, for example, the prevention, amelioration, or prophylaxis of an autoimmune disease or inflammatory condition. The compound of the present disclosure can be administered as a pharmaceutical composition comprising a therapeutically effective amount of the compound together with a pharmaceutically acceptable carrier. In the context of the present disclosure, a "therapeutically effective amount" is understood as the amount of a compound inhibiting the synthesis, expression, and/or activity of an identified HA polymer that is necessary to achieve the desired effect which, in this specific case, is treating an autoimmune disease or disorder, in particular, multiple sclerosis. Generally, the therapeutically effective amount of the compound according to the present disclosure to be administered will depend, among other factors, on the individual to be treated, on the severity of the disease the individual suffers, on the chosen dosage form, and the like. For this reason, the doses mentioned in the present disclosure must be considered only as a guideline for a person skilled in the art, and the skilled person must adjust the doses according to the previously mentioned variables. Nonetheless, a compound according to the present disclosure can be administered one or more times a day, for example, 1, 2, 3 or 4 times a day, in a typical total daily amount comprised between 0.1 µg to 10,000 mg/day, typically 100 to 1,500 mg/day.

The subject can be a human or non-human animal, a vertebrate, and is typically an animal, including but not limited to, cows, pigs, horses, chickens, cats, dogs, and the like. More typically, the subject is a mammal, and in a particular embodiment, human.

As used herein, an "autoimmune disease" is a disease or disorder arising from and directed against an individual's own tissues. Examples of autoimmune diseases or disorders include, but are not limited to, multiple sclerosis, arthritis (rheumatoid arthritis, juvenile rheumatoid arthritis, psoriatic arthritis), conditions involving infiltration of T-cells and chronic inflammatory responses, autoimmune myocarditis, pemphigus, Type 1 diabetes (also referred to as autoimmune diabetes or insulin-dependent diabetes mellitus (IDDM)), autoimmune lung disease, and the like.

As used herein, the term "a mammalian subject suffering from autoimmune diabetes" refers to a subject suffering from an autoimmune disease that results in a high blood glucose level which can lead to serious problems with the heart, eyes, kidneys, nerves, and gums and teeth. Symptoms of autoimmune diabetes include, for example, being very thirsty, urinating often, feeling very hungry or tired, losing weight without trying, having sores that heal slowly, having dry, itchy skin, losing the feeling in the feet or having tingling in the feet, and/or having blurry eyesight.

As used herein, the term "a mammalian subject suffering from multiple sclerosis" refers to a subject suffering from an autoimmune disease that results in damage to the insulating covers of nerve cells in the brain and spinal cord or demyelination. Symptoms of MS include numbness or weakness in one or more limbs, partial or complete loss of central vision, usually in one eye, often with pain during eye movement (optic neuritis), double vision or blurring of vision, tingling or pain in parts of the body, electric-shock sensations that occur with certain head movements, tremor, lack of coordination or unsteady gait, slurred speech, fatigue, dizziness, and/or heat sensitivity, among others.

As used herein the term "treating" or "treatment" means the administration of a compound according to the disclosure to effectively prevent, repress, or eliminate at least one symptom associated with MS. Preventing at least one symptom associated with MS involves administering a treatment to a subject prior to onset of the symptoms associated with clinical disease. Repressing at least one symptom associated with MS involves administering a treatment to a subject after clinical appearance of the disease.

As noted above, HA is a polymer of disaccharides composed of glucuronic acid and N-acetylglucosamine and linked via alternating β-1,4 and β-1,3 glycosidic bonds. 4-MU functions as a competitive substrate for UGT, an enzyme involved in the synthesis of HA as well as bile (Kakizaki, I., et al., *J. Biol. Chem.* 279, 33281-33289 (2004)). 4-MU is used throughout Europe and Asia to prevent gallstones. It has been used for more than 30 years in both children and adults and has an excellent safety profile. It is available without prescription in the USA as a dietary supplement primarily marketed for use in people suffering from jaundice.

Figure 1B:
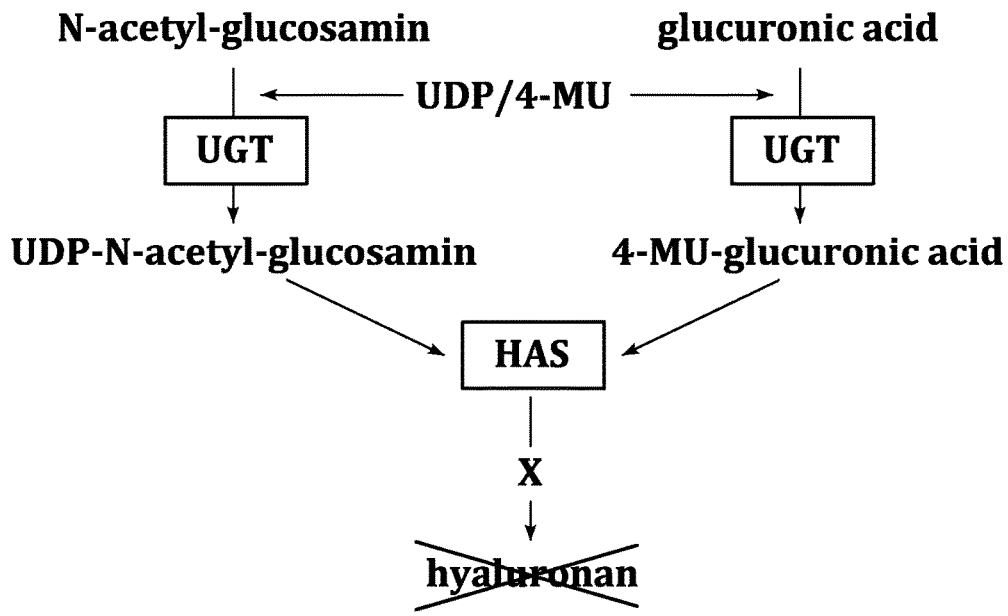
FIG. 1B illustrates a mechanism of 4-MU interference and depicts 4-MU binding to glucuronic acid instead of UDP.

FIGS. 1A and 1B describe mechanisms of HA synthesis and 4-MU interference, respectively. Specifically, FIG. 1A shows the normal way HA is synthesized. The compound 4-MU is known to bind to glucuronic acid, and FIG. 1B shows how 4-MU binds to glucuronic acid instead of UDP. Because of the binding of 4-MU to a critical HA precursor, the enzymes that produce HA, the HA-synthases (HAS), cannot synthesize HA.

As described below, it was unexpectedly discovered that 4-MU has the surprising property of reversing autoimmune inflammation. This finding was made in a mouse model of autoimmune diabetes and MS. 4-MU is also an inhibitor of HA synthesis and the data suggest that this property, rather than its effects on biliary metabolism, is responsible for the anti-inflammatory properties of 4-MU. This mechanism of action is consistent with a central role for HA as an inflammatory mediator.

Data described herein indicate that 4-MU has applicability as a novel, first-in-class anti-inflammatory drug that targets HA synthesis. Further, these data support the use of 4-MU to abrogate autoimmune, allergic, and atopic diseases. Because 4-MU has no known toxicity, it has great potential in treating and preventing autoimmune diseases, including but not limited to autoimmune diabetes, multiple sclerosis, Sjögrens disease, autoimmune thyroiditis, Lupus, rheumatoid arthritis, psoriasis, colitis, asthma, allergy, and the like.

Recent reports (Bollyky, P. L., et al. (2012), supra; Hull, R. L., et al., supra) identify a critical role for HA in mediating insulitis and in the progression to autoimmune diabetes. In those works, it was shown that large deposits of HA characterize mice with autoimmune diabetes but not mice treated with streptozotocin, a therapy toxic to beta cells (Bollyky et al. (2012), supra) or to healthy, non-diabetic mice (Hull et al., supra). It has since been found that human diabetes is likewise associated with HA deposits in islets with insulitis, but that such deposits were not seen in non-diabetics. FIGS. 2A, 2B, 2C, and 2D relate to HA staining in pancreatic islets from autoimmune diabetes human cadaveric donors. FIG. 2A shows representative HA staining of an islet from human donors without autoimmune diabetes. FIG. 2B shows representative HA staining of an islet from human donors with autoimmune diabetes. FIG. 2C shows representative higher magnification of intra-islet HA accumulation from human donors without autoimmune diabetes. FIG. 2D shows representative higher magnification of intra-islet HA accumulation from human donors with autoimmune diabetes.

In order to identify the role of HA in autoimmune diabetes, the amount and distribution of HA in pancreatic islets was identified. Further, the changes in HA that accompany autoimmune islet destruction in a T1D mouse model were characterized. The inventors determined that HA accumulates in the pancreatic islets and creates a permissive environment for autoimmune attacks during autoimmune diabetes disease progression.

To determine that HA accumulates in the pancreatic islets and creates a permissive environment for autoimmune attacks during autoimmune diabetes disease progression, the DORmO double transgenic mouse model of autoimmune diabetes was used. DORmO mice predictably develop autoimmune diabetes because they are bred to have both a target antigen on their insulin producing beta-cells as well as an immune system that specifically recognizes that antigen. DORmO mice are the result of a cross between RIPmOVA mice (a strain that carries a gene specific for hen egg ovalbumin (OVA) that is only expressed on beta-cells, emulating the auto-antigen) and DO11.10 mice (a strain that carries a T-cell receptor transgene specific for OVA, emulating auto-reactive CD4+ T cells). DORmO mice spontaneously develop autoimmune insulitis starting at four weeks of age and all animals become diabetic (hyperglycemia >200 mg/dl) by 20 weeks of age (Wesley, J. D., et al., *J. Immunol.* 185, 4760-4768 (2010) (see, e.g., FIG. 4, below). DORmO mice have spontaneous autoimmunity which closely parallels the inflammatory beta-cell destruction found in humans.

Figure 3:
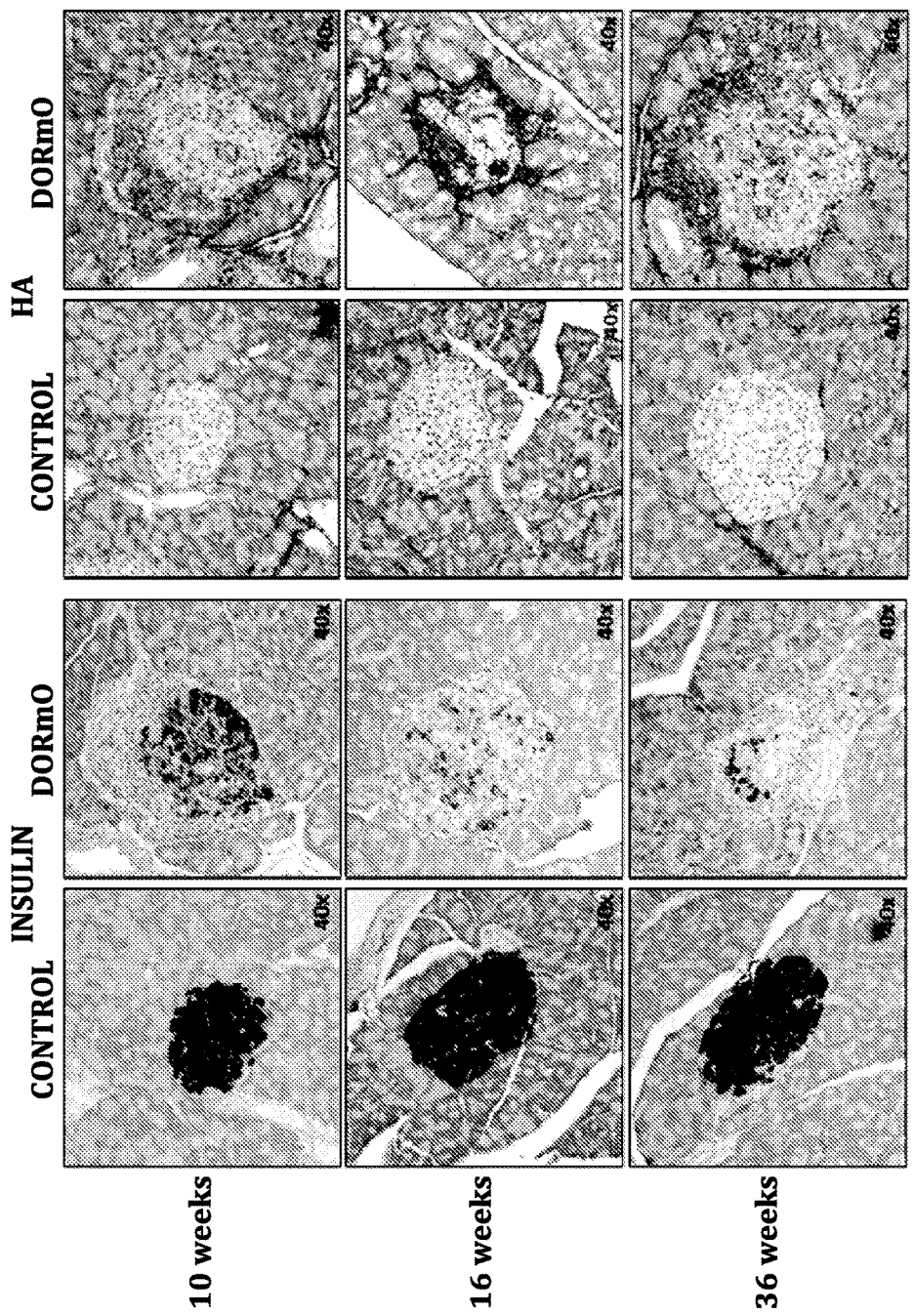
FIG. 3 shows insulin and HA staining in pancreatic islets from control and DORmO mice at three different time points during autoimmune diabetes progression. The far left column shows representative insulin staining of islets from control mice at 10, 16 and 36 weeks of age. The second left column shows representative insulin staining of islets from DORmO mice at these same ages. The third column from the left shows representative HA staining of islets from control mice. The far right column shows representative HA staining of islets from DORmO mice also at 10, 16 and 36 weeks of age.

The findings from the human cadaveric donors were reproduced in the DORmO mice. Insulitis in this model was found to be accompanied by an expected decrease of insulin and with a dramatic increase in HA. The HA distribution inside the islet was mainly around the invading cells and the microvasculature. FIG. 3 shows insulin and HA staining in pancreatic islets from control and DORmO mice at three different time points during autoimmune diabetes progression. The far left column shows representative insulin staining of islets from control mice at 10, 16 and 36 weeks of age. The second left column shows representative insulin staining of islets from DORmO mice at these same ages. The third column from the left shows representative HA staining of islets from control mice. The far right column shows representative HA staining of islets from DORmO mice also at 10, 16 and 36 weeks of age.

Figure 4:
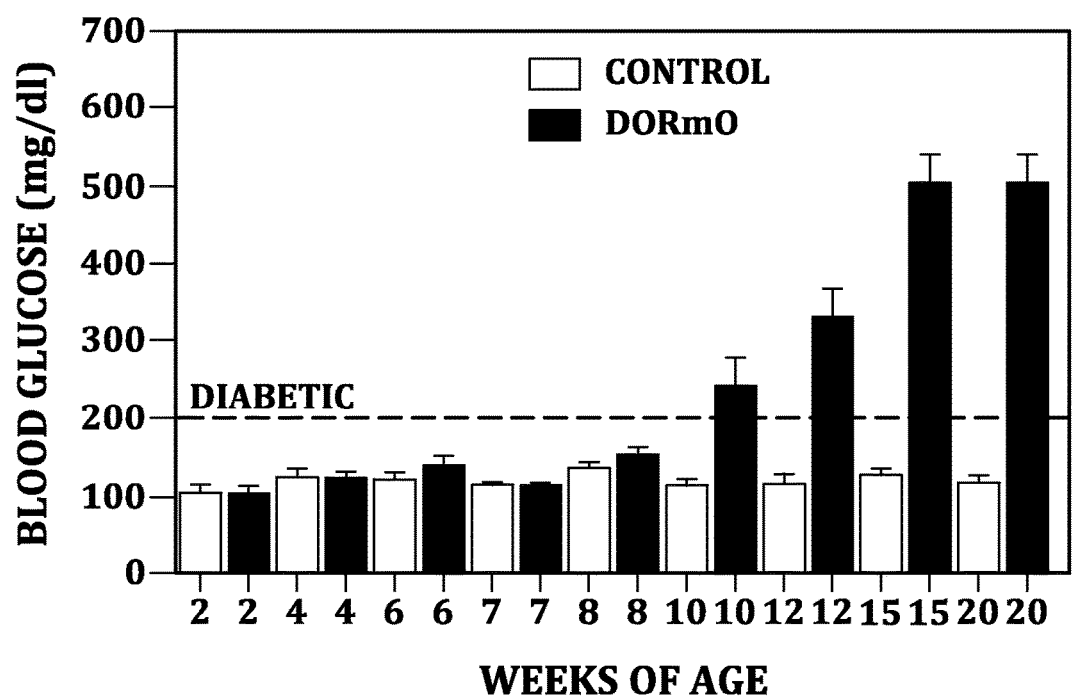
FIG. 4 shows blood glucose levels of control and DORmO mice during the progression of autoimmune diabetes. The white bars indicate the control mice and the black bars indicate the DORmO mice. The solid horizontal line labeled "diabetic" shows the amount of blood glucose where mice are considered hyperglycemic in this study. The blood glucose of the mice was monitored between 2 and 20 weeks of age.

FIG. 4 shows blood glucose levels of control and DORmO mice during the progression of autoimmune diabetes. The white bars indicate the control mice and the black bars indicate the DORmO mice. The solid horizontal line labeled "diabetic" shows the amount of blood glucose where mice are considered hyperglycemic in this study. The blood glucose of the mice was monitored between 2 and 20 weeks of age.

Taken together, these data indicate that alterations in HA accompany the invasion and destruction of islet tissue by T cells and create a permissive environment for autoimmune attacks. These data demonstrate that HA directed therapies can be used to treat and prevent autoimmune diabetes.

The first DORmO treatment groups were started with 4-MU at 5 weeks of age, when the mice have normal blood glucose levels. Four (4) different treatment groups were established, control mice on normal chow, control mice on 4-MU, DORmO mice on normal chow and DORmO mice on 4-MU. A group of control mice was treated with 4-MU as well in order to see if 4-MU alters the blood glucose levels of those mice.

Figure 5:
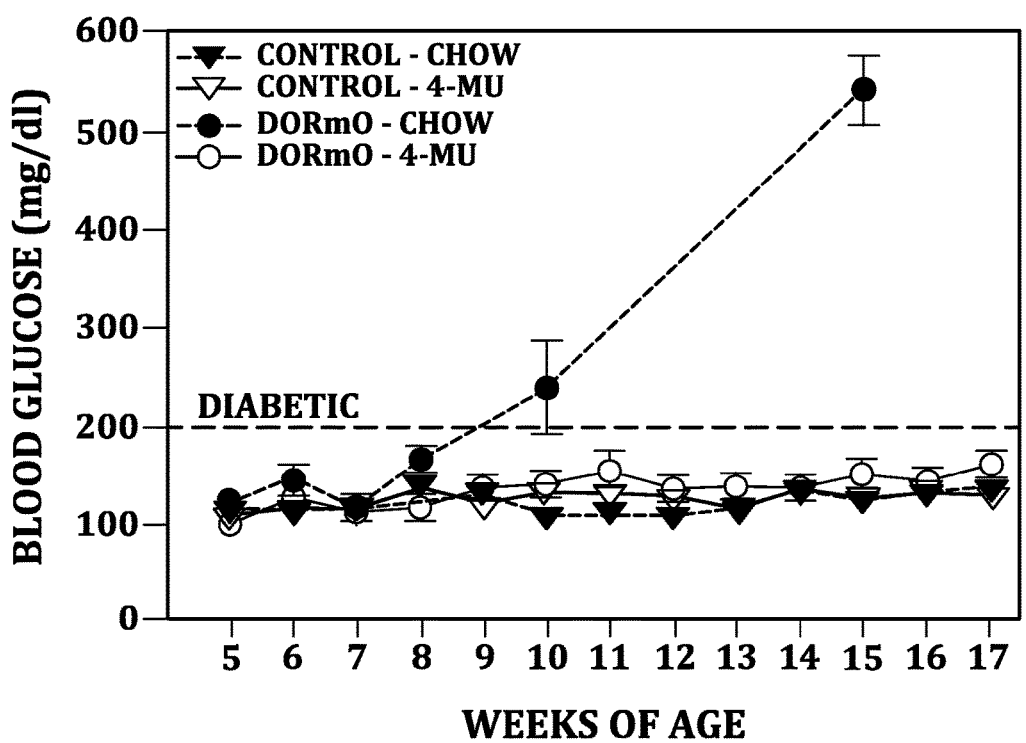
FIG. 5 shows blood glucose data from control and DORmO mice, with and without 4-MU treatment starting at 5 weeks of age. The solid horizontal line labeled "diabetic" shows the amount of blood glucose where mice are considered hyperglycemic.
Figure 6:
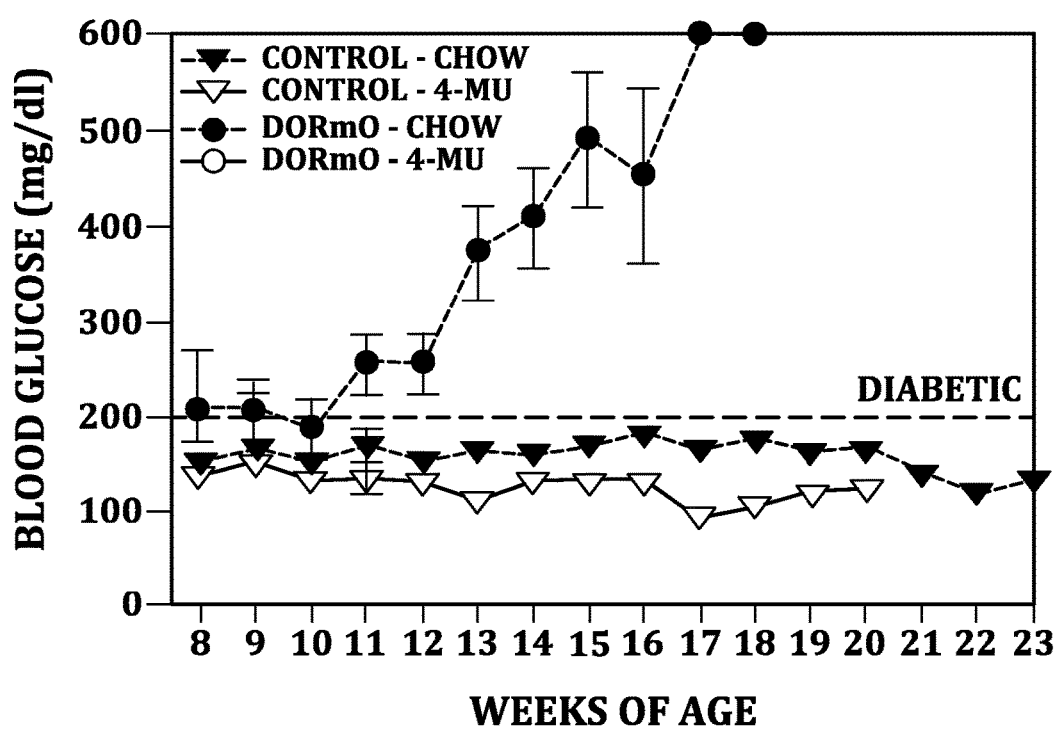
FIG. 6 shows blood glucose data from control and DORmO mice, with and without 4-MU treatment starting at 8 weeks of age. The solid horizontal line labeled "diabetic" shows the amount of blood glucose where mice are considered hyperglycemic.

FIG. 5 shows blood glucose data from control and DORmO mice, with and without 4-MU treatment starting at 5 weeks of age. The solid horizontal line labeled "diabetic" shows the amount of blood glucose where mice are considered hyperglycemic. Referring to FIG. 5, the DORmO-4-MU line appears below the horizontal line labeled "diabetic." Accordingly, the DORmO mice on 4-MU were demonstrated not to become diabetic because their blood glucose level is on the control level. Further, it was observed that 4-MU does not alter the blood glucose level of the control animals After this surprising finding, another 4-MU treatment group was initiated starting at 8 weeks of age, closer to the age where the DORmO mice become diabetic with similar results to the 5 week treatment group start. FIG. 6 shows blood glucose data from control and DORmO mice, either with or without 4-MU treatment starting at 8 weeks of age. The solid horizontal line labeled "diabetic" shows the amount of blood glucose where mice are considered hyperglycemic. The DORmO mice on 4-MU treatment reached 23 weeks of age and still had a normal blood glucose level. The DORmO mice on control chow had to be sacrificed after getting diabetic according to the animal protocol.

Figure 7:
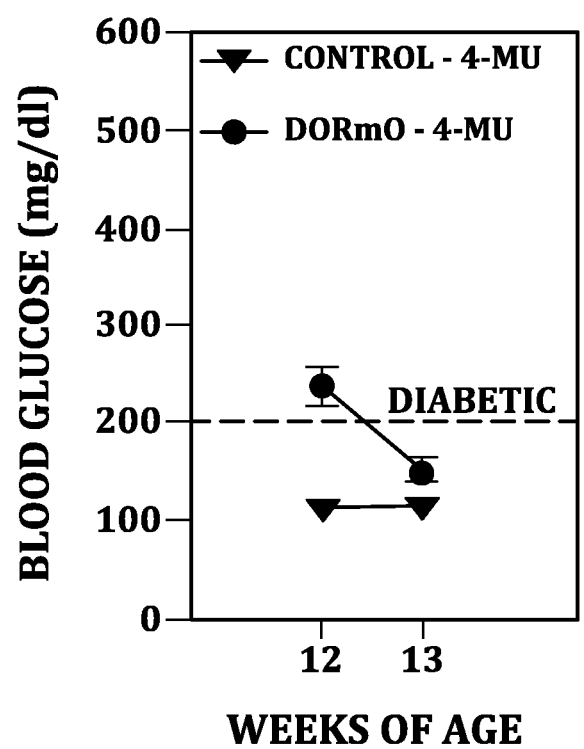
FIG. 7 shows blood glucose data from control and DORmO mice, with 4-MU treatment starting at 12 weeks of age. The solid horizontal line labeled "diabetic" shows the amount of blood glucose where mice are considered hyperglycemic.

Another treatment group was established where the 4-MU treatment started at 12 weeks of age when the DORmO mice were already diabetic. FIG. 7 shows blood glucose data from control and DORmO mice, with 4-MU treatment starting at 12 weeks of age. The solid horizontal line labeled "diabetic" shows the amount of blood glucose where mice are considered hyperglycemic. A decrease of the blood glucose levels of the 4-MU treated DORmO mice was observed after only 1 week of treatment, indicating that even established autoimmune diabetes can be reversed by 4-MU.

Figure 8:
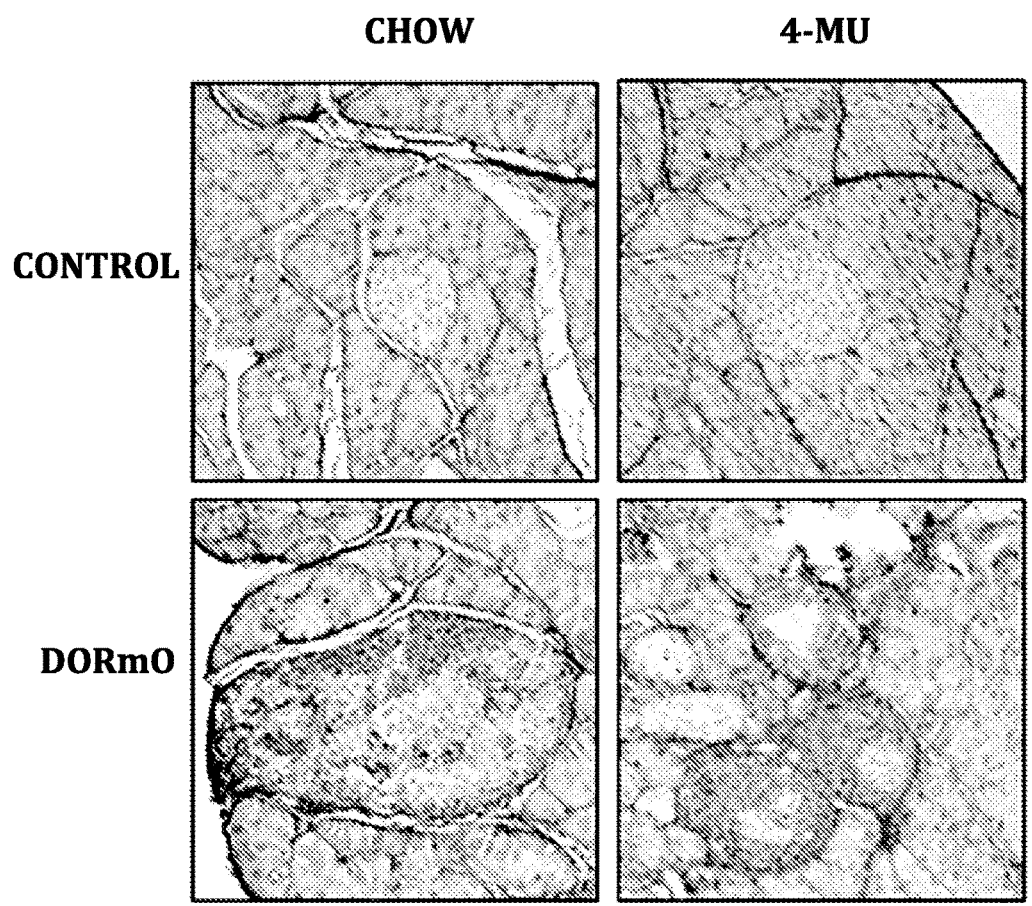
FIG. 8 shows immuno-staining for HA in pancreatic islets of control and DORmO mice with and without 4-MU treatment. The pictures in the upper row show representative images of a HA staining in pancreatic islets in control animals treated with normal chow, left column, or treated with 4-MU, right column. The lower row shows representative images of DORmO pancreatic islets stained for HA, where animals were treated with control chow, left column, or treated with 4-MU, right column.
Figure 9:
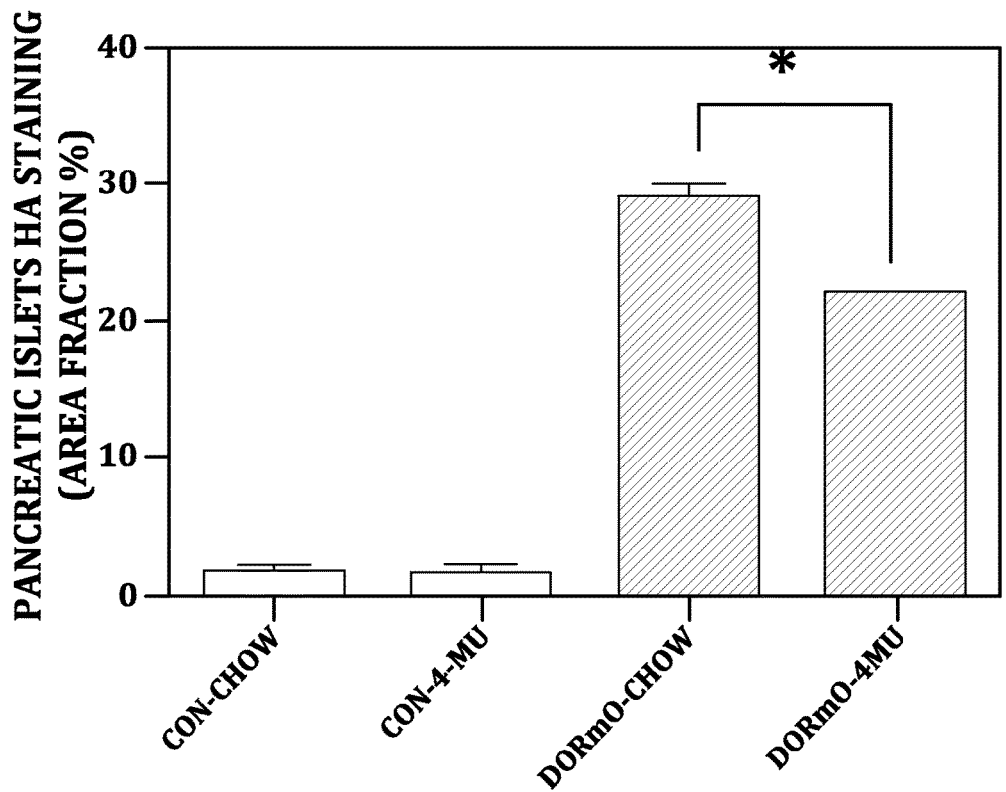
FIG. 9 shows an evaluation of the HA staining in the pancreatic islet between the different treatment groups. *<0.05 was considered significant.
Figure 10:
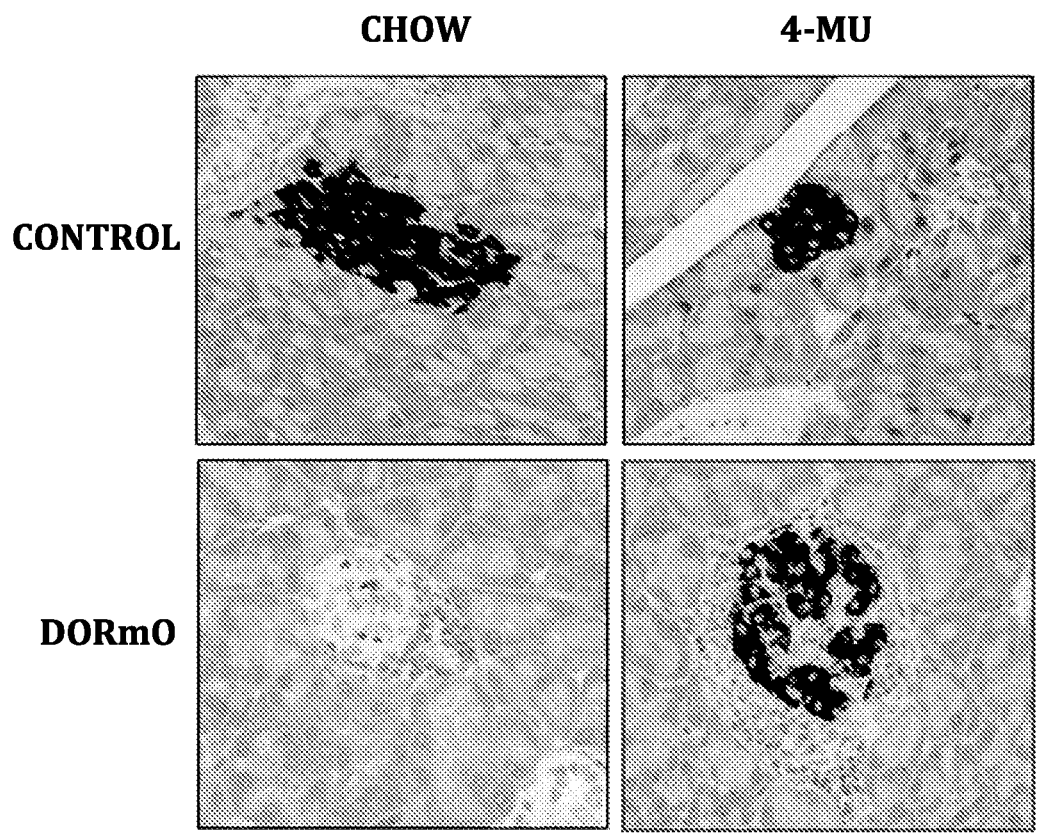
FIG. 10 shows immuno-staining for insulin in pancreatic islets of control and DORmO mice with and without 4-MU. The pictures in the upper row show representative images of insulin staining in pancreatic islets in control animals treated with normal chow, (left column) or treated with 4-MU (right column). The lower row shows representative images of DORmO pancreatic islets stained for insulin, where animals were treated with control chow (left column) or treated with 4-MU (right column).

HA accumulation in the pancreatic islets was investigated through immuno-staining after 4-MU treatment in a few mice of the 8 week start treatment group. FIG. 8 shows immuno-staining for HA in pancreatic islets of control and DORmO mice with and without 4-MU treatment. The pictures in the upper row show representative images of a HA staining in pancreatic islets in control animals treated with normal chow, left column, or treated with 4-MU, right column. The lower row shows representative images of DORmO pancreatic islets stained for HA, where animals were treated with control chow, left column, or treated with 4-MU, right column. A significant decrease in the HA accumulation was found in the DORmO mice treated with 4-MU in contrast to the DORmO mice treated with control chow. FIG. 9 shows an evaluation of the HA staining in the pancreatic islet between the different treatment groups. *<0.05 was considered significant The animals stained for HA were also stained for insulin. FIG. 10 shows immuno-staining for insulin in pancreatic islets of control and DORmO mice with and without 4-MU. The pictures in the upper row show representative images of insulin staining in pancreatic islets in control animals treated with normal chow (left column), or treated with 4-MU (right column). The lower row shows representative images of DORmO pancreatic islets stained for insulin, where animals were treated with control chow (left column) or treated with 4-MU (right column). The DORmO mice treated with 4-MU still had a significant amount of insulin in the islets, which is enough to maintain the blood glucose on the control level. In addition, when 4-MU was added to chow it was determined that 4-MU restored normo-glycemia in DORmO mice.

Thus, it has been discovered that 4-MU has the surprising property of reversing autoimmune diseases and disorders, in this specific instance, for example, autoimmune diabetes.

The extracellular matrix polysaccharide HA is a key inflammatory mediator known to be abundant in demyelinating lesions in multiple sclerosis as well as in the mouse model of the disease, EAE. As described herein, inhibition of HA synthesis can prevent EAE. The data indicate that treatment with a UDP-glycosyltransferase inhibitor, such as a UDP-glucuronyltransferase (UGT) inhibitor, for example 4-MU or a metabolite of 4-MU, has the capacity to not only block the induction of EAE but also substantially reduce clinical deficits in already established EAE. Preliminary studies suggest that treatment with a UDP-glycosyltransferase inhibitor, such as a UGT inhibitor, for example 4-MU or a metabolite of 4-MU, skews the immune response towards an anti-inflammatory profile characterized by increased numbers of FoxP3+ regulatory T-cells (Treg), an important cell population known to prevent autoimmunity.

UDP-glycosyltransferase is an enzyme that catalyzes the transfer of a sugar moiety from a UDP-sugar to a wide range of metabolites such as hormones and secondary metabolites. Generally, UDP-glycosyltransferase acts in the final step of biosynthetic pathway in order to increase solubility, stability, storage, bioactivity, or biological availability of metabolites. One type of UDP-glycosyltransferase is UGT, an enzyme that catalyzes the transfer of the glucuronic acid component of UDP-glucuronic acid to a small hydrophobic molecule in a glucuronidation reaction.

Competitive inhibition is a form of enzyme inhibition where binding of the inhibitor to the active site on the enzyme prevents binding of the substrate and vice versa. Substrates that are specific for certain UGT isoforms can be used as specific inhibitors to identify UGT isoforms responsible for the glucuronidation of drugs. Known UGT inhibitors include, for example, Atazanavir, Gemfibrozil, Indinavir, Ketoconazole, Ketoconazole, and Valproic acid, among others.

Metabolites of 4-MU can be effective to skew the immune response towards an anti-inflammatory profile characterized by increased numbers of FoxP3+ regulatory T-cells (Treg). Metabolites of 4-MU are described in, for example, Kakizaki, I., et al., *J. Biol. Chem.* 279, 33281-33289 (2004), and in Garrett, E. R., et al., *Biopharm. Drug Dispos.* 14, 13-39 (1994), both of which are incorporated herein by reference.

Exemplary metabolites of 4-MU include 4-MUG and 4-MUS. In order to determine serum levels of 4-MU in blood over a 24 hour period from 4-MU arising from dietary chow intake, Balb/C female mice (12-week old purchased from Taconic Farms) were placed on a 5% 4-MU containing chow diet (n=18) or non-4-MU containing control chow (n=3). Mice were weighed at the start of the experiment and at two week endpoint. At two weeks, blood was collected by cardiac puncture with heparinized syringes, placed in collection tubes on ice, spun down and plasma frozen at −80° C. Plasma samples were subsequently analyzed by gas chromatography-mass spectrometry (GCMS) for 4-MU and two 4-MU conjugates, 4-MUG and 4-MUS.

Figure 11A:
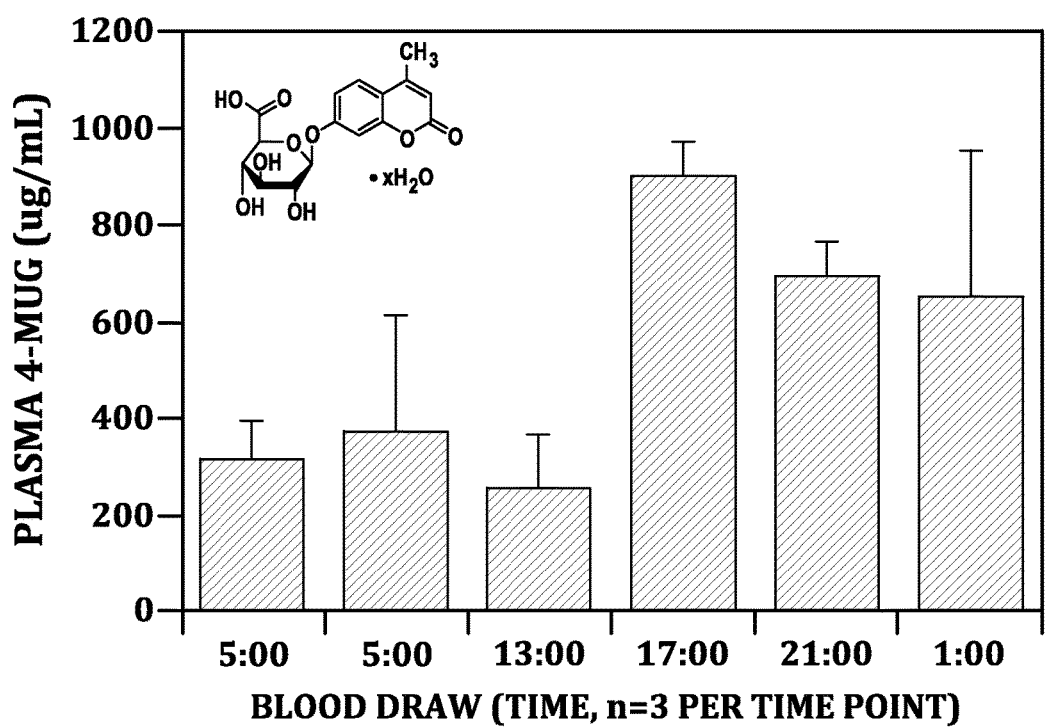
FIG. 11A is a graphical representation showing a concentration of plasma 4-MU-glucuronide (4-MUG) for a series of timed blood draws.
Figure 11B:
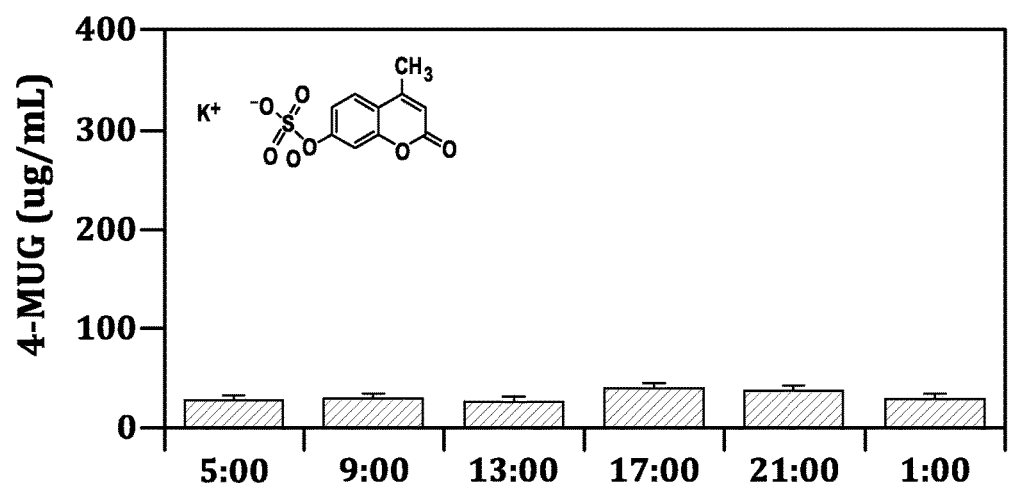
FIG. 11B is a graphical representation showing a concentration of plasma sulfated 4-MU (4-MUS) for a series of timed blood draws.
Figure 11C:
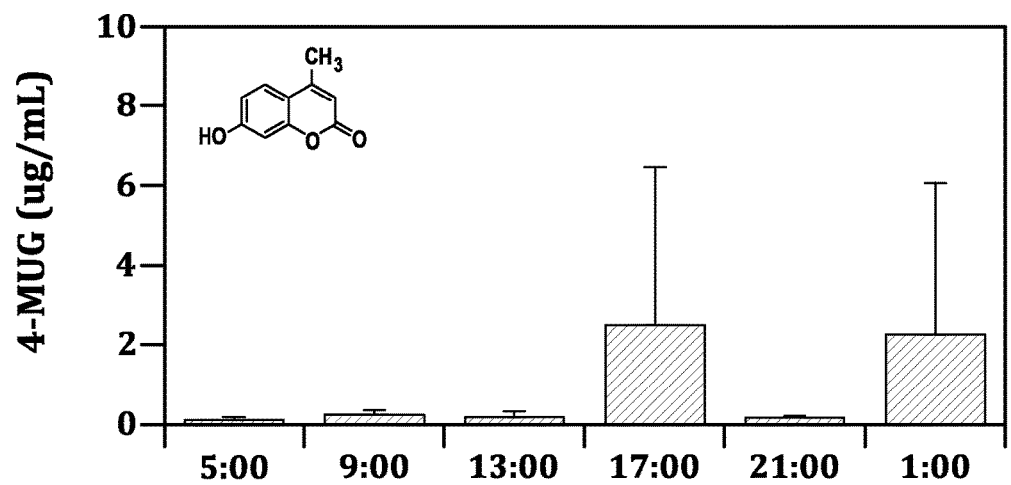
FIG. 11C is a graphical representation showing a concentration of plasma 4-MU for a series of timed blood draws.

FIGS. 11A, 11B, and 11C show plasma levels of 4-MUG, 4-MUS, and unconjugated 4-MU in mice following a 14-day solid food diet containing 5% 4-MU. Blood was collected every 4 hours over a 24 hour period (n=3 mice per time point). The most dominant plasma product is 4-MUG and was undetectable in mice on control chow (data not shown). As anticipated, 4-MUG levels were higher during the night time (7 PM to 7 AM in the vivarium) when mice are known to be feeding more. 4-MU and 4-MUS were present, though, at much lower levels. Neither 4-MU nor 4-MUS were detectable in control chow fed mice. Twenty-four hour average levels of 4-MU (0.9 µg/mL) and the sulfated product 4-MUS (30.5 µg/mL) were present at about 600 and 20 fold lower levels respectively relative to 4-MUG (513 µg/mL). The results demonstrate that Balb/C mice on a 2-week 5% 4-MU containing chow diet show a 24-hour average 4-MUG blood plasma level of about 500 µg/mL, with much lower levels of the 4-MUS conjugate and the unconjugated 4-MU, and confirm that 4-MUG and 4-MUS are metabolites of 4-MU.

Given the reports that HA deposits are abundant in CNS lesions and that this is primarily LMW-HA, it was hypothesized that HA could drive immune dysregulation at these sites. To test this hypothesis the effects of a selective inhibitor of HA synthesis, 4-MU, in the EAE mouse model of MS were assessed.

Figure 12A:
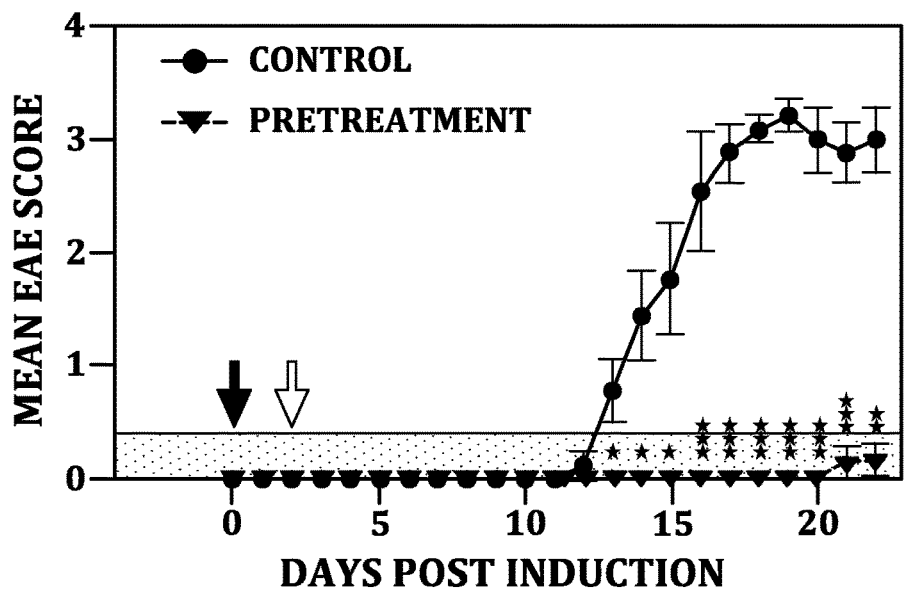
FIG. 12A is a graphical representation showing mean EAE score as a function of days post induction in subjects treated with 4-MU before induction of disease (pretreatment protocol).
Figure 12B:
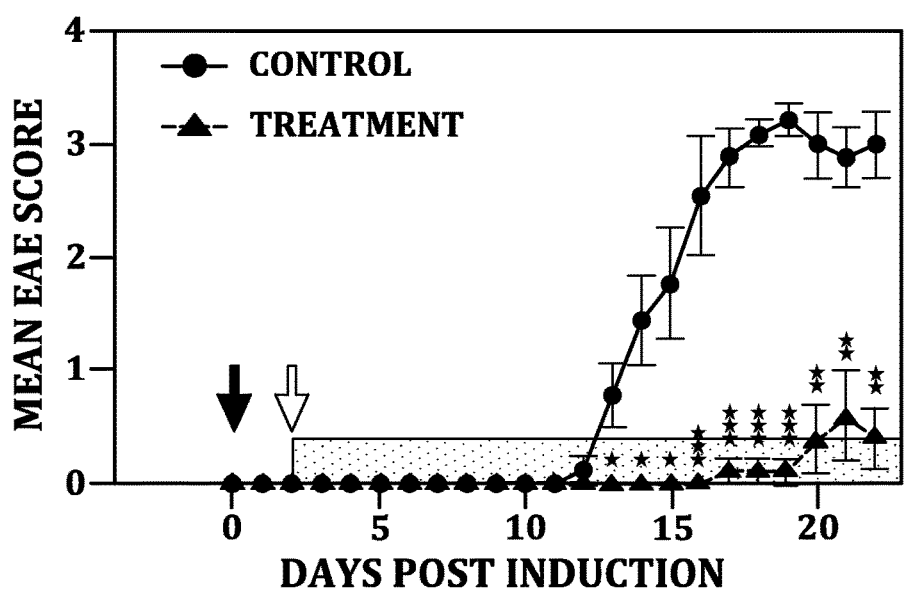
FIG. 12B is a graphical representation showing mean EAE score as a function of days post induction in subjects treated with 4-MU after induction of disease but before onset of symptoms (treatment protocol).
Figure 12C:
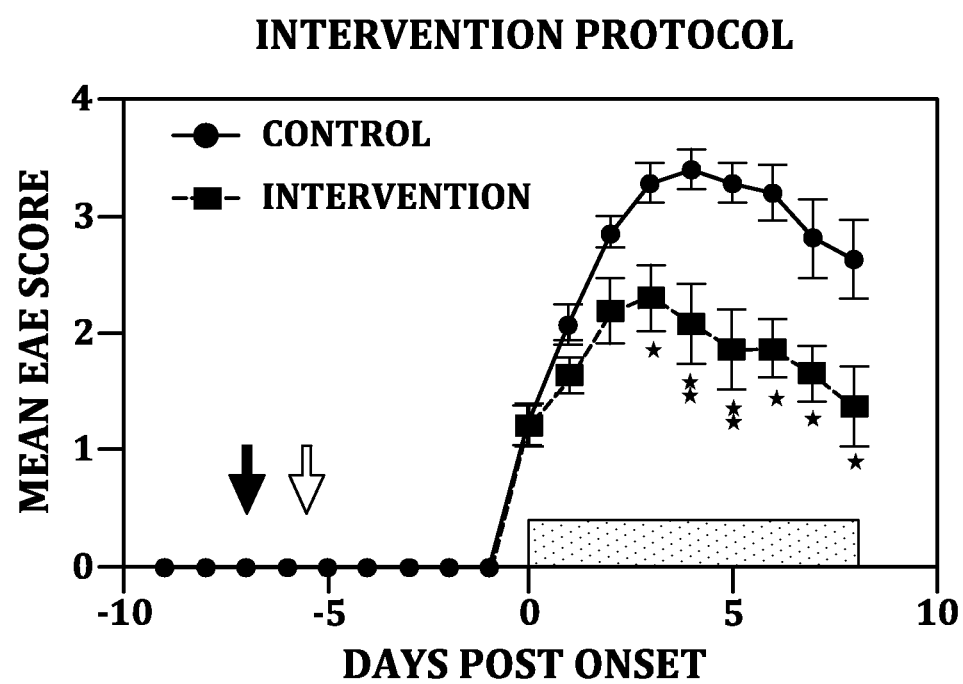
FIG. 12C is a graphical representation showing mean EAE score as a function of days post induction in subjects treated with 4-MU after onset of disease (intervention protocol).

To confirm the pathogenic role of HA in MS, EAE was induced in C57Bl/6 mice by immunization with myelin oligodendrocyte glycoprotein peptide fragment 35-55 ($MOG_{35-55}$) and the mice were treated with a previously established safe dose of 4-MU in the chow, starting either 4 days before immunization (pretreatment protocol), immediately following the immunization boost on day 2 (treatment protocol) or when animals showed signs of neurological defects (intervention protocol). FIGS. 12A, 12B, and 12C graphically illustrate the mean EAE score as a function of days post induction in subjects treated with 4-MU according to a pretreatment, treatment, or intervention protocol, respectively.

As shown in FIGS. 12A and 12B, treatment with 4-MU (5% w/w in the chow) before induction of disease (pretreatment protocol, FIG. 12A) or after induction of disease, but before the onset of symptoms (treatment protocol, FIG. 12B), dramatically reduced the incidence and severity of $MOG_{35-55}$ peptide-induced EAE in C57Bl/6 mice (1/7 and 2/10 vs. 9/10 control treated animals, respectively). As shown in FIG. 12C, treatment with 4-MU after the onset of neurological symptoms (intervention protocol) significantly ameliorated disease as early as 3 days after start of treatment and reduced the severity of EAE. For FIGS. 12A, 12B, and 12C, * $P<0.05$,  $P<0.01$, * $P<0.001$, Mann-Whitney.

The data demonstrate that inhibition of HA synthesis interferes with immune activation mechanisms leading to, as well as ongoing in, neurological pathology. Further, the data demonstrate that 4-MU treatment prevents disease progression and reduces established disease in EAE subjects.

Thus, in one aspect, a composition for treating an autoimmune, allergic, or atopic disease comprising (i) a compound that inhibits hyaluronan synthesis, and (ii) a pharmaceutically acceptable carrier is described.

The term "pharmaceutically acceptable carrier" as used herein means one or more compatible solid or liquid filler, diluents or encapsulating substances which are suitable for administration to a subject. The components of the pharmaceutical compositions also are capable of being commingled with each other, in a manner such that there is no interaction, which would substantially impair the desired pharmaceutical efficiency. Such preparations can routinely contain pharmaceutically acceptable concentrations of salt, buffering agents, preservatives, compatible carriers, adjuvants and optionally other therapeutic ingredients.

Suitable liquid or solid pharmaceutical preparation forms are, for example, aqueous or saline solutions for inhalation, microencapsulated, encochleated, coated onto microscopic gold particles, contained in liposomes (including pH-dependent release formulations), lipidoids, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of the compositions, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249, 1527-1533 (1990) and Langer and Tirrell, *Nature* 428, 487-492 (2004). In addition, the compositions described herein can be formulated as a depot preparation, time-release, delayed release or sustained release delivery system.

In one embodiment, the compound is a UDP-glycosyltransferase inhibitor. In one embodiment, the compound is a UDP-glucuronyltransferase inhibitor. In one embodiment, the compound is 4-methylumbelliferone or a metabolite of 4-methylumbelliferone, for example, 4-methylumbelliferone-glucuronide or a sulfated 4-methylumbelliferone.

Figure 13A:
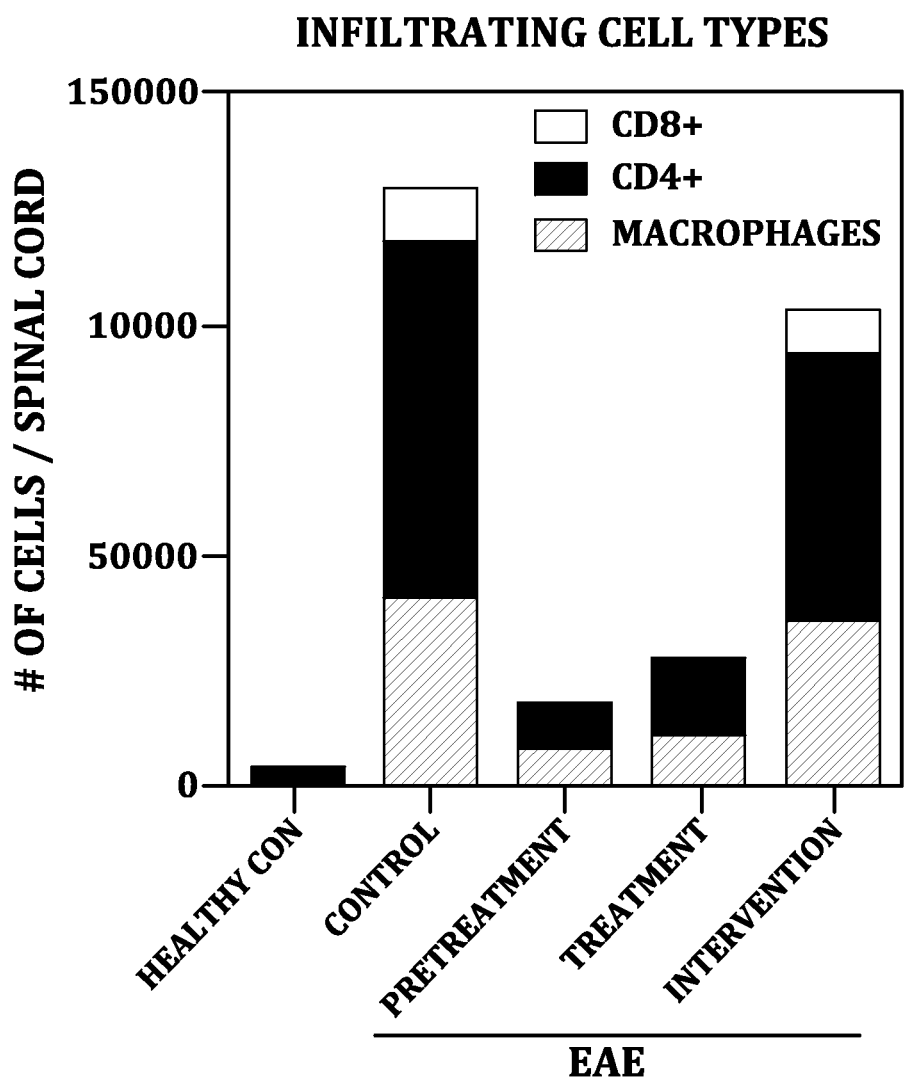
FIG. 13A is a graphical representation of infiltrating cell types depicting the number of CD8+ and CD4+ lymphocytes, as well as macrophages, in healthy control, control, pretreatment, treatment, and intervention protocol subjects.

The effect of 4-MU treatment on EAE pathogenesis was analyzed by evaluating the immunologic profile of cells infiltrating into the spinal cord at the peak of disease (day 22 after immunization). The total number of infiltrates correlated with disease score and consisted mainly of CD4+ T-cells, which were substantially reduced by pretreatment and early treatment with 4-MU, whereas intervention treatment moderately reduced CD4+ T-cell infiltration. FIG. 13A relates to infiltrating cell types and shows the number of CD8+ and CD4+ lymphocytes, as well as macrophages, in healthy control, control, pretreatment, treatment, and intervention protocol subjects. As shown in FIG. 13A, 4-MU treatment resulted in lower total numbers of cell infiltrates, and reduced infiltration of CD8+ and CD4+ lymphocytes, as well as macrophages. Surprisingly, 4-MU did not cause generalized immunosuppression or a general increase in lymphocyte proliferation in these animals, considering the observation that total lymphocyte counts in lymphatic organs were unchanged.

Figure 13B:
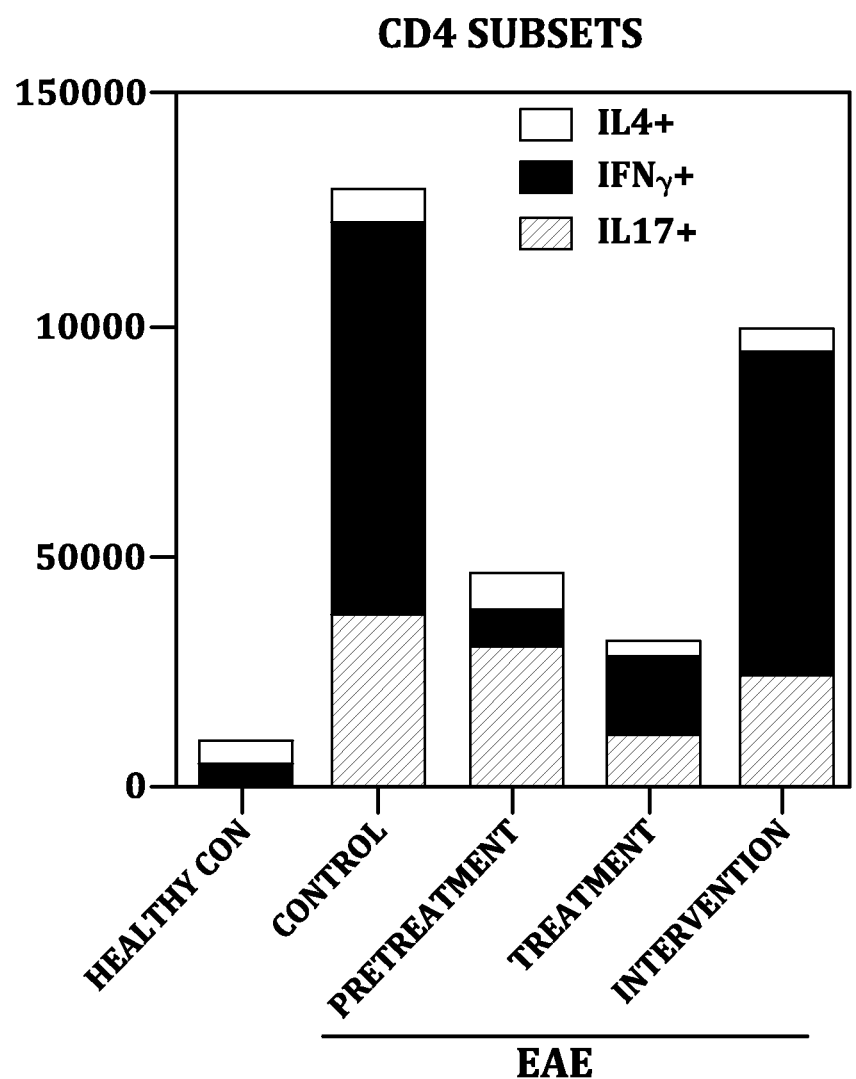
FIG. 13B is a graphical representation depicting the number IL4+, IFN-γ+ and IL17+ cells in healthy control, control, pretreatment, treatment, and intervention protocol subjects within the CD4+ population.

FIG. 13B shows the number IL4+, IFN-γ+, and IL17+ cells in healthy control, control, pretreatment, treatment, and intervention protocol subjects within the CD4+ population. Interestingly, upon further analysis of the CD4+ T-cells that were still present in the CNS after 4-MU treatment, 4-MU treatment mainly reduced the IFN-γ producing Th1 populations, correlating with reduction of disease severity whereas the IL-17 producing Th17 population was less affected. This last observation shows that 4-MU treatment skews the T-cell profiles of infiltrating lymphocytes in the CNS by skewing the local Th balance away from a Th1 response. Further, considering the differential pathologic roles that Th1 and Th17 cells have in EAE (Axtell, R. C., et al., *Clin. Rev. Allergy Immunol.* 44, 114-120 (2013); Lowther, D. E., et al., *Acta Neuropathol.* 126, 501-515 (2013)), this change in the local Th cell profile can contribute to the prevention of the autoimmune attack on myelin.

Figure 13C:
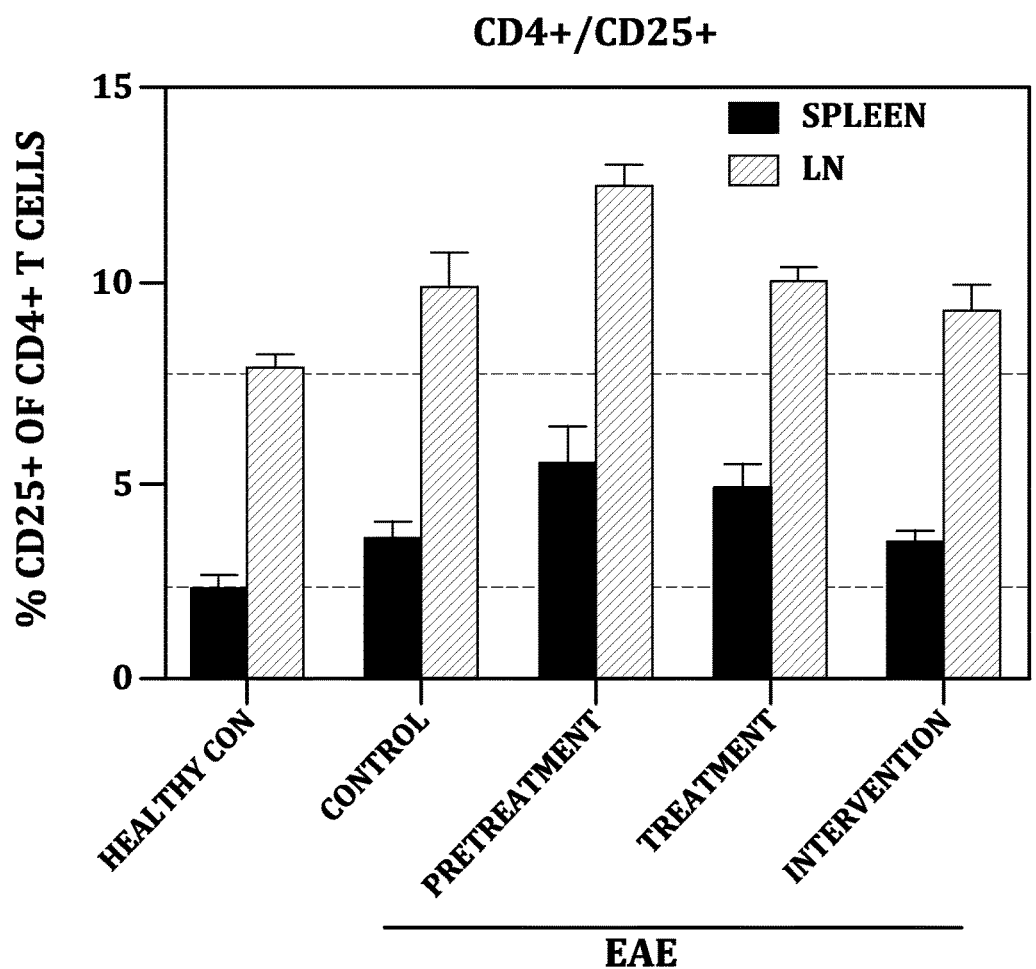
FIG. 13C is a graphical representation of showing the percentage of CD25+ of CD4+ T-cells in the spleen and lymph nodes of healthy control, control, pretreatment, treatment, and intervention protocol subjects.

Considering that the reduced infiltration of T-cells into the spinal cord can be due to the induction of a regulatory mechanism by 4-MU, the role of 4-MU treatment in inducing possible regulatory cells in secondary lymphoid organs was assessed by analyzing the number of CD25+ T-cells. FIG. 13C shows the percentage of CD25+ of CD4+ T-cells in the spleen and lymph nodes of healthy control, control, pretreatment, treatment, and intervention protocol subjects. As shown in FIG. 13C, 4-MU treatment started in EAE subjects before immunization (pretreatment protocol) resulted in an increased number of CD4+CD25+ cells in the spleen and lymph nodes. However, because CD25 is generally induced upon activation, the effect of 4-MU on the induction of a possible Treg population was further evaluated by analyzing the induction of FoxP3+ T-cells.

Figure 13D:
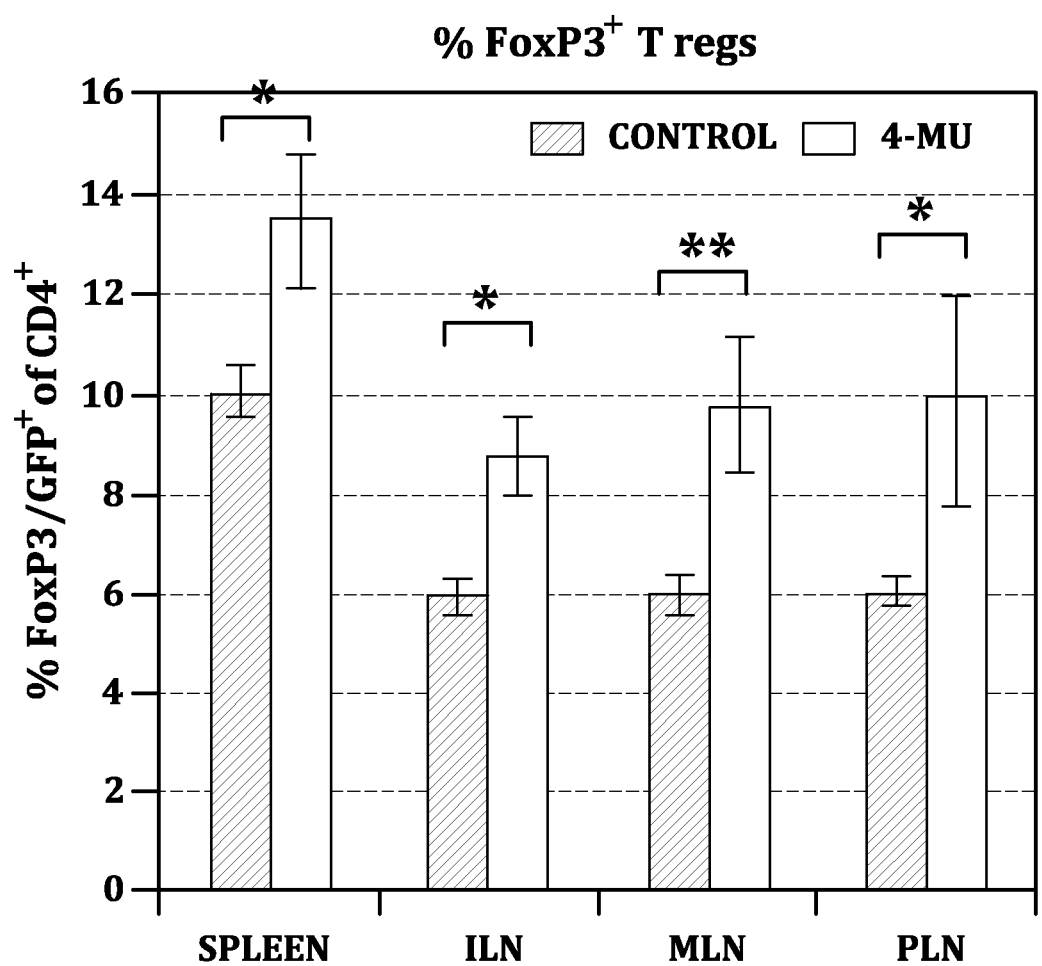
FIG. 13D is a graphical representation of the percentage of FoxP3+CD4+ T-cells in spleen, inguinal lymph nodes (ILN), mesenteric lymph nodes (MLN), and pancreatic lymph nodes (PLN) in control and 4-MU treated subjects.

First, using healthy mice, it was observed that 4-MU treatment significantly increased numbers of FoxP3+ T-cells in lymphatic tissue (data not shown). FIG. 13D shows the percentage of FoxP3+CD4+ T-cells in control and 4-MU treated subjects. As shown in FIG. 13D, by analyzing Treg numbers following OVA immunization in D0.11 mice, an increase in FoxP3+ T-cells in multiple immunologic compartments, including the spleen, mesenteric lymph nodes (MLN), inguinal lymph nodes (ILN), and pancreatic lymph nodes (PLN) was observed, demonstrating that 4-MU induces a Treg response. As in the EAE mice, it was confirmed that 4-MU treatment did not induce a general immunosuppression in these mice (data not shown).

Thus, in one embodiment, the compound is effective to induce a regulatory T-cell response. In one embodiment, the compound is effective to increase FoxP3+ regulatory T cells.

In one embodiment, the autoimmune, allergic, or atopic disease is selected from the group consisting of autoimmune diabetes, multiple sclerosis, Sjögrens disease, autoimmune thyroiditis, Lupus, rheumatoid arthritis, psoriasis, colitis, and asthma. In one embodiment, the autoimmune, allergic, or atopic disease is autoimmune diabetes or multiple sclerosis.

In one aspect, a method for treating an autoimmune, allergic, or atopic disease in a mammalian subject in need thereof is provided. The method comprises administering to the subject a composition comprising a compound in an amount effective to inhibit hyaluronan synthesis in the mammalian subject is provided. In one embodiment, the compound is a UDP-glycosyltransferase inhibitor. In one embodiment, the compound is a UDP glucuronyltransferase inhibitor. In one embodiment, the compound is 4-methylumbelliferone or a metabolite of 4-methylumbelliferone, for example, 4-methylumbelliferone-glucuronide or a sulfated 4-methylumbelliferone.

In one embodiment of the method, the compound is effective to induce a regulatory T-cell response. In one embodiment, the compound is effective to increase FoxP3+ regulatory T-cells.

In one embodiment, the mammalian subject is a human subject. In one embodiment, the human subject is suffering from, or at risk for developing an autoimmune, allergic, or atopic disease selected from the group consisting of autoimmune diabetes, multiple sclerosis, Sjögrens disease, autoimmune thyroiditis, Lupus, rheumatoid arthritis, psoriasis, colitis, and asthma.

In one aspect, a method for treating insulitis and/or reversing progression of autoimmune diabetes in a mammalian subject suffering from or at risk of developing autoimmune diabetes is described. The method comprises administering to the mammalian subject a composition comprising a compound in an amount effective to inhibit hyaluronan synthesis in the mammalian subject.

In one embodiment, the compound is a UDP-glycosyltransferase inhibitor or a UDP glucuronyltransferase inhibitor. In one embodiment, the compound is 4-methylumbelliferone or a metabolite of 4-methylumbelliferone. In one embodiment, the mammalian subject is a human subject.

The mode of administration can be any medically acceptable mode including oral administration, sublingual administration, intranasal administration, intratracheal administration, inhalation, ocular administration, topical administration, transdermal administration, intradermal administration, rectal administration, vaginal administration, subcutaneous administration, intravenous administration, intramuscular administration, intraperitoneal administration, intrasternal, administration, or via transmucosal administration. In addition, modes of administration can be via an extracorporeal device and/or tissue-penetrating electro-magnetic device.

The particular mode selected will depend upon the particular compound selected, the desired results, the particular condition being treated and the dosage required for therapeutic efficacy. The methods described herein, generally speaking, can be practiced using any mode of administration that is medically acceptable, for example, any mode that produces effective levels of inflammatory response alteration without causing clinically unacceptable adverse effects.

The compositions can be provided in different vessels, vehicles or formulations depending upon the disorder and mode of administration. For example, for oral application, the compositions can be administered as sublingual tablets, gums, mouth washes, toothpaste, candy, gels, films, etc.; for ocular application, as eye drops in eye droppers, eye ointments, eye gels, eye packs, as a coating on a contact lens or an intraocular lens, in contacts lens storage or cleansing solutions, etc.; for topical application, as lotions, ointments, gels, creams, sprays, tissues, swabs, wipes, etc.; for vaginal or rectal application, as an ointment, a tampon, a suppository, a mucoadhesive formulation, and the like.

The compositions can be administered by injection, e.g., by bolus injection or continuous infusion, via intravenous, subcutaneous, intramuscular, intraperitoneal, intrasternal routes. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. For oral administration, the compositions can be formulated readily by combining the compositions with pharmaceutically acceptable carriers well known in the art, e.g., as a sublingual tablet, a liquid formulation, or an oral gel.

For administration by inhalation, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin, for use in an inhaler or insufflator can be formulated containing a powder mix of the compositions and a suitable powder base such as lactose or starch. Medical devices for the inhalation of therapeutics are known in the art. In some embodiments the medical device is an inhaler. In other embodiments the medical device is a metered dose inhaler.

The compositions can also be formulated in rectal or vaginal compositions such as suppositories or retention enemas, e.g., containing conventional suppository bases such as cocoa butter or other glycerides.

Figure 14A:
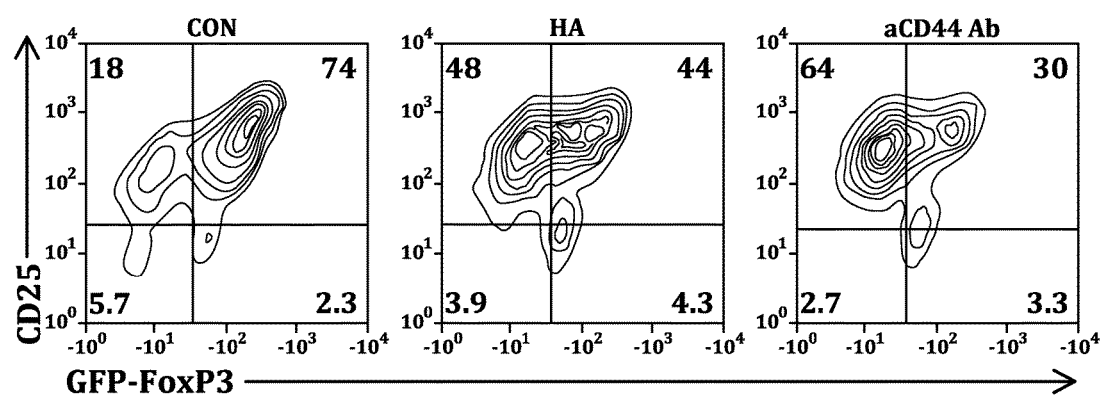
FIG. 14A is a graphical representation of CD25 and FoxP3 expression by CD4+GFP/FoxP3− T-cells activated for 72 hours in the presence of TGFβ and IL-2 with or without plate-bound high molecular weight HA (HMW-HA) or a CD44 antibody.

Because inhibition of HA synthesis by a UDP glycosyltransferase inhibitor, or a UGT inhibitor, or 4-MU treatment promotes FoxP3 induction, the role of HA and signaling through its receptor CD44 in the regulation of FoxP3 expression was investigated. FIG. 14A shows CD25 and FoxP3 expression by CD4+GFP/FoxP3− T-cells activated for 72 hours in the presence of TGFβ and IL-2 with or without plate-bound HMW-HA or a CD44 antibody. As shown in FIG. 14A, using GFP/FoxP3 reporter mice, the plate-coated HA and anti-CD44 antibody were observed to strongly diminish FoxP3 induction from CD4+GFP/FoxP3 precursors in vitro. In addition, in vitro Treg induction using CD4+GFP/FoxP3− T-cells isolated from CD44$^{−/−}$ mice yielded higher numbers of FoxP3 expressing Tregs than cells isolated from CD44$^{+/+}$ or CD44$^{−/+}$ mice, demonstrating a reduction in FoxP3 induction inversely proportional to the number of CD44+ alleles expressed.

Figure 14B:
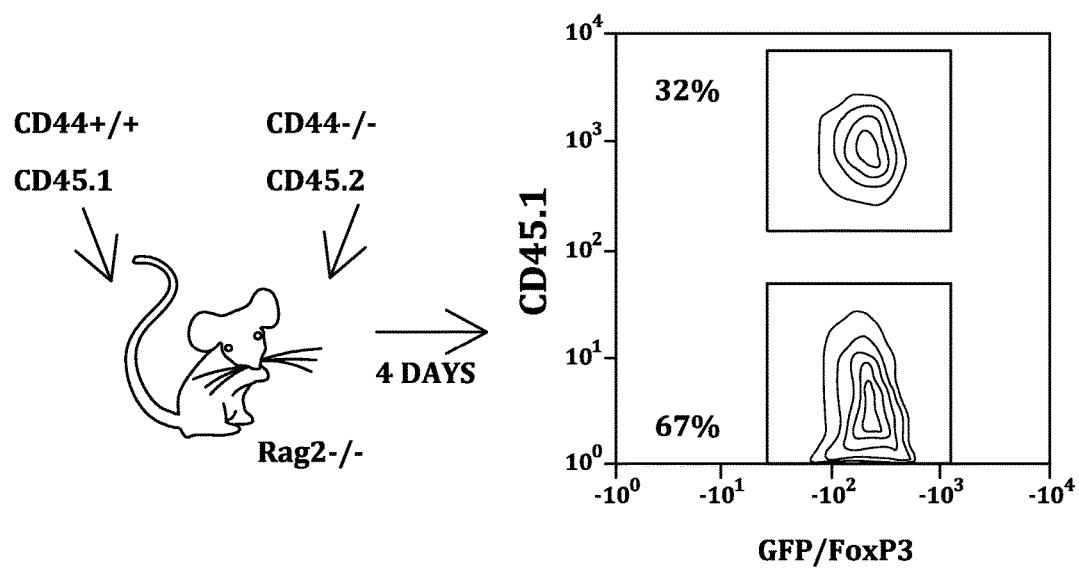
FIG. 14B is a representative plot depicting the ratio of CD44−/− (CD45.1) vs. CD44+/+(CD45.2) T-cells for 3 RAG−/− recipient subjects.
Figure 14C:
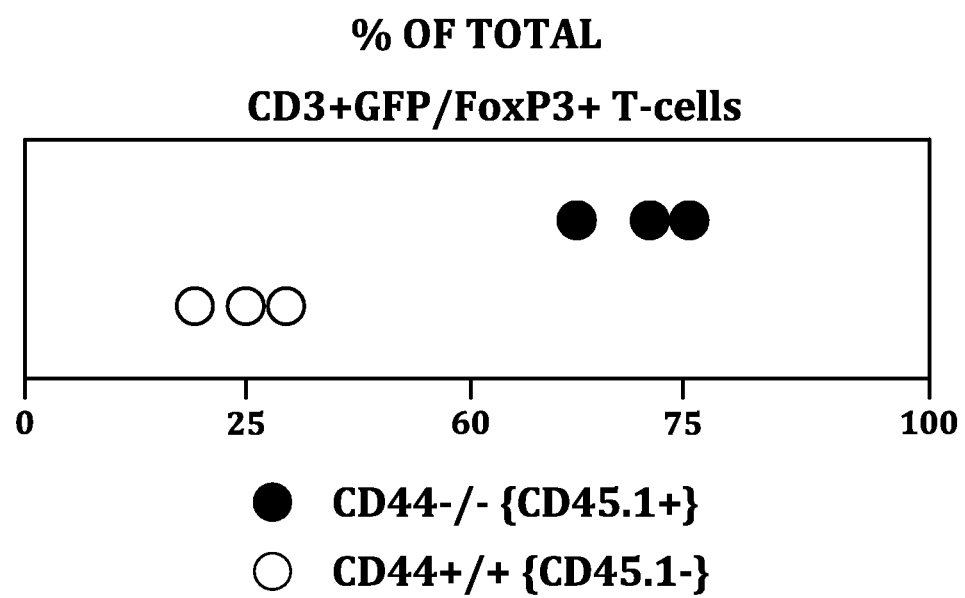
FIG. 14C is a graphical representation showing the percent of total CD3+GFP/FoxP3+ T-cells for 3 RAG−/− recipient subjects.

FIG. 14B relates to in vivo induction of FoxP3 after co-transfer of equivalent numbers of GFP/FoxP3−CD4+−CD44+/+−CD45.1 and GFP/FoxP3−CD4+CD44−/−CD45.2 T-cells into RAG−/− hosts. The number of CD3+GFP/FoxP3+ T-cells was assessed 4 days after transfer and the ratio of CD44−/−(CD45.1) vs. CD4+/+(CD45.2) T-cells was determined. FIG. 14C shows cumulative data for the 3 RAG−/− recipient animals.

As shown in FIGS. 14B and 14C, co-transfer of equivalent numbers of GFP/FoxP3−CD4$^+$CD44$^{+/+}$CD45.1 and GFP/FoxP3−CD4$^+$CD44$^{−/−}$CD45.2 T-cells into RAG$^{−/−}$ hosts revealed that CD44$^{−/−}$ CD4+ cells (CD45.1$^−$) gave rise to a larger population of FoxP3+ cells, indicating the reduced potential of CD44 expressing CD4 T-cells to develop into FoxP3+ Tregs. Together these data indicate that HMW-HA and CD44 suppress FoxP3 induction in vitro and in vivo, and that CD44 signaling is an important inhibitory signal in Treg induction.

Taken together, the data show that increased levels of HA can create an environment that promotes autoimmunity by inhibiting the induction of FoxP3+ Treg. Furthermore, the data show that 4-MU treatment can block the autoimmune attack on myelin in MS.

Thus, in one aspect, a method for treating multiple sclerosis and/or autoimmune demyelination in a mammalian subject suffering from or at risk of developing multiple sclerosis is provided. The method comprises administering to the mammalian subject a composition comprising a compound in an amount effective to inhibit hyaluronan synthesis in the mammalian subject. In one embodiment, the compound is a UDP-glycosyltransferase inhibitor or a UDP glucuronyltransferase inhibitor. In one embodiment, the compound is 4-methylumbelliferone or a metabolite of 4-methylumbelliferone. In one embodiment, the mammalian subject is a human subject.

In one embodiment of the method, the compound is effective to induce a regulatory T-cell response. In one embodiment, the compound is effective to increase FoxP3+ regulatory T-cells.

Some of the work described herein was supported in part by Deutsche Forschungsgemeinschaft (DFG) under project number NA 965/2-1.

While the preferred embodiments have been illustrated and described, it will be appreciated that various changes can be made therein without departing from the spirit and scope of the claimed subject matter.

The embodiments of the invention in which an exclusive property or privilege is claimed are defined as follows:

1. A method for ameliorating an autoimmune, allergic, or atopic disease in a subject in need thereof comprising:
   administering to the subject a therapeutically effective amount of
   4-methylumbelliferone, a metabolite of 4-methylumbelliferone, 4-methylumbelliferone-glucuronide, or a sulfated 4-methylumbelliferone;
   wherein hyaluronan synthesis in the subject is inhibited after said administering step; and
   wherein the disease is not rheumatoid arthritis or lupus.

2. The method of claim 1, comprising inducing a regulatory T-cell response.

3. The method of claim 2, comprising increasing FoxP3+ regulatory T-cells.

4. The method of claim 1, wherein the subject is a human subject.

5. The method of claim 4, wherein disease is selected from the group consisting of autoimmune diabetes, multiple sclerosis, Sjögrens disease, autoimmune thyroiditis, psoriasis, colitis, and asthma.

6. The method of claim 1, wherein the compound is formulated for oral administration.

7. The method of claim 2, wherein the compound is formulated for oral administration.

8. A method for ameliorating an autoimmune, allergic, or atopic disease in a subject in need thereof, comprising:

inducing a regulatory T-cell response or increasing FoxP3+ regulatory cells in said subject;
wherein a therapeutically effective amount of a compound induces a regulatory T-cell response or increases FoxP3+ regulatory cells;
wherein the compound is 4-methylumbelliferone or a metabolite of 4-methylumbelliferone; and
inhibiting hyaluronan synthesis in the subject after said inducing or increasing step;
wherein the disease is not rheumatoid arthritis or lupus.

9. The method of claim 8, wherein the subject is a human subject.

10. A method for ameliorating multiple sclerosis or autoimmune demyelination in a subject in need thereof comprising:
administering to the subject a therapeutically effective amount of a compound that inhibits hyaluronan synthesis in the subject,
wherein the compound is 4-methylumbelliferone or a metabolite of 4-methylumbelliferone;
wherein the compound is formulated for oral administration, sublingual administration, intranasal administration, intratracheal administration, inhalation, ocular administration, topical administration, transdermal administration, intradermal administration, rectal administration, vaginal administration, subcutaneous administration, intravenous administration, intramuscular administration, intraperitoneal administration, intrasternal administration, or transmucosal administration, or via an extracorporeal device and/or tissue-penetrating electro-magnetic device; and
wherein the administering is not to the central nervous system (CNS).

11. The method of claim 10, wherein the subject is a human subject.

12. The method of claim 10, comprising inducing a regulatory T-cell response.

13. The method of claim 12, comprising increasing FoxP3+ regulatory T-cells.

14. A method of ameliorating lupus in a subject in need thereof comprising:
administering to the subject a therapeutically effective amount of a metabolite of 4-methylumbelliferone that ameliorates lupus;
wherein the metabolite of 4-methylumbelliferone is 4-methylumbelliferone-glucuronide or a sulfated 4-methylumbelliferone; and
wherein hyaluronan synthesis in the subject is inhibited after said administering step.

15. The method of claim 14, wherein the subject is a human subject.

16. The method of claim 14, comprising inducing a regulatory T-cell response.

17. The method of claim 16, comprising increasing FoxP3+ regulatory T-cells.

18. The method of claim 14, wherein the compound is formulated for oral administration.

19. A method of ameliorating rheumatoid arthritis in a subject in need thereof comprising:
administering to the subject a therapeutically effective amount of a metabolite of 4-methylumbelliferone that ameliorates the rheumatoid arthritis;
wherein the metabolite of 4-methylumbelliferone is 4-methylumbelliferone-glucuronide or a sulfated 4-methylumbelliferone;
wherein hyaluronan synthesis in the subject is inhibited after said administering step.

20. The method of claim 19, wherein the subject is a human subject.

21. The method of claim 19, comprising inducing a regulatory T-cell response.

22. The method of claim 21, comprising increasing FoxP3+ regulatory T-cells.

23. The method of claim 19, wherein the compound is formulated for oral administration.

* * * * *